US012558327B2

(12) United States Patent　　(10) Patent No.:　US 12,558,327 B2
Montemurro et al.　　　　　　　　(45) Date of Patent:　　Feb. 24, 2026

(54) METHODS AND COMPOSITIONS FOR TREATING SLEEP APNEA

(71) Applicant: The Brigham and Women's Hospital, Inc., Boston, MA (US)

(72) Inventors: Luigi Taranto Montemurro, Brookline, MA (US); D. Andrew Wellman, Wayland, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 1044 days.

(21) Appl. No.: 17/428,596

(22) PCT Filed: Feb. 7, 2020

(86) PCT No.: PCT/US2020/017323
§ 371 (c)(1),
(2) Date: Aug. 4, 2021

(87) PCT Pub. No.: WO2020/163785
PCT Pub. Date: Aug. 13, 2020

(65) Prior Publication Data
US 2022/0096401 A1　　Mar. 31, 2022

Related U.S. Application Data

(60) Provisional application No. 62/803,223, filed on Feb. 8, 2019.

(51) Int. Cl.
*A61K 31/138*　　　(2006.01)
*A61K 31/195*　　　(2006.01)
(Continued)

(52) U.S. Cl.
CPC .......... *A61K 31/138* (2013.01); *A61K 31/437* (2013.01); *A61K 31/4468* (2013.01);
(Continued)

(58) Field of Classification Search
CPC ................ A61K 31/138; A61K 31/437; A61K 31/4468; A61K 31/497; A61K 31/5375;
(Continued)

(56) References Cited

U.S. PATENT DOCUMENTS

| 6,294,582 B1 | 9/2001 | Jerussi |
| 11,123,313 B2 | 9/2021 | Wellman et al. |
(Continued)

FOREIGN PATENT DOCUMENTS

| CN | 1396829 A | 2/2003 |
| CN | 101132777 A | 2/2008 |
(Continued)

OTHER PUBLICATIONS

Patel N, LeWitt P, Neikrug AB, Kesslak P, Coate B, Ancoli-Israel S. Nighttime Sleep and Daytime Sleepiness Improved With Pimavanserin During Treatment of Parkinson's Disease Psychosis. Clin Neuropharmacol. Nov./Dec. 2018;41(6):210-215. (Year: 2018).*
(Continued)

*Primary Examiner* — Bruck Kifle
*Assistant Examiner* — Kevin S Martin
(74) *Attorney, Agent, or Firm* — Fish & Richardson P.C.

(57) ABSTRACT
Methods and compositions for the treatment of conditions associated with pharyngeal airway muscle collapse while the subject is in a non-fully conscious state, e.g., sleep apnea and snoring, comprising administration of (i) a norepinephrine reuptake inhibitor (NRI) and (ii) a non myorelaxing hypnotic and/or 5-HT2A inverse agonist or antagonist.

7 Claims, 7 Drawing Sheets

(51) Int. Cl.

| | |
|---|---|
| *A61K 31/437* | (2006.01) |
| *A61K 31/4468* | (2006.01) |
| *A61K 31/497* | (2006.01) |
| *A61K 31/5375* | (2006.01) |
| *A61K 31/551* | (2006.01) |
| *A61P 25/00* | (2006.01) |
| *A61K 31/496* | (2006.01) |
| *A61K 45/06* | (2006.01) |
| *A61P 11/00* | (2006.01) |
| *A61P 25/20* | (2006.01) |

(52) U.S. Cl.

CPC ........ *A61K 31/497* (2013.01); *A61K 31/5375* (2013.01); *A61P 25/00* (2018.01)

(58) Field of Classification Search

CPC .... A61K 45/06; A61K 31/551; A61K 31/195; A61K 31/496; A61K 2300/00; A61P 25/00; A61P 11/00; A61P 25/20

See application file for complete search history.

(56) References Cited

U.S. PATENT DOCUMENTS

| | | | |
|---|---|---|---|
| 2002/0010216 A1 | 1/2002 | Rogosky et al. | |
| 2002/0155113 A1 | 10/2002 | Chun et al. | |
| 2006/0039866 A1 | 2/2006 | Rao et al. | |
| 2006/0039867 A1 | 2/2006 | Rao et al. | |
| 2007/0219201 A1 | 9/2007 | Carroll, Jr. et al. | |
| 2008/0181943 A1 | 7/2008 | Cuine et al. | |
| 2009/0169620 A1 | 7/2009 | Venkatesh et al. | |
| 2010/0029770 A1 | 2/2010 | Roberts et al. | |
| 2010/0204058 A1 | 8/2010 | Chang et al. | |
| 2014/0323423 A1 | 10/2014 | DiPierro et al. | |
| 2018/0296565 A1 | 10/2018 | Hsu | |
| 2020/0054583 A1 | 2/2020 | Wellman et al. | |
| 2021/0401777 A1 | 12/2021 | Wellman et al. | |
| 2024/0189261 A1 | 6/2024 | Wellman et al. | |
| 2024/0261239 A1 | 8/2024 | Wellman et al. | |

FOREIGN PATENT DOCUMENTS

| | | | | |
|---|---|---|---|---|
| CN | 103458899 A | 12/2013 | | |
| EA | 2008/00618 A1 | 6/2008 | | |
| WO | WO 2003/039436 | 5/2003 | | |
| WO | WO 2004/060366 | 7/2004 | | |
| WO | WO 2006/055854 | 5/2006 | | |
| WO | WO 2006/069030 | 6/2006 | | |
| WO | WO 2008/122019 | 10/2008 | | |
| WO | WO 2008/124128 | 10/2008 | | |
| WO | WO-2008157094 A1 * | 12/2008 | ......... | A61K 31/4402 |
| WO | WO 2016/062285 | 4/2016 | | |
| WO | WO 2016/176177 | 11/2016 | | |
| WO | WO 2016/201373 | 12/2016 | | |
| WO | WO 2018/200775 | 11/2018 | | |
| WO | WO 2019/152475 | 8/2019 | | |
| WO | WO 2020/163785 | 8/2020 | | |

OTHER PUBLICATIONS

ID Office Action in Indonesian Appln. No. P00202106608, dated Mar. 9, 2023, 5 pages (with English translation).

Curado et al., "Pharmacotherapy of obstructive sleep apnea: is salvation just around a corner?," American Journal of Respiratory and Critical Care Medicine, May 15, 2019, 199(10):1186-7.

EA Office Action in Eurasian Appln. No. 202192202, dated Dec. 14, 2022, 13 pages (with English translation).

Jullian-Desayes et al., "Impact of concomitant medications on obstructive sleep apnoea," British Journal of Clinical Pharmacology, Apr. 2017, 83(4):688-708.

NZ Office Action in New Zealand Appln. No., 758564, dated Dec. 6, 2022, 6 pages.

Patel et al., "Nighttime sleep and daytime sleepiness improved with pimavanserin during treatment of Parkinson's disease psychosis," Clinical Neuropharmacology, Nov. 1, 2018, 41(6):210-5.

SG Office Action in Singaporean Appln. No. 11202108225Q, dated Dec. 20, 2022, 14 pages.

Barnes, "Muscarinic receptor subtypes in airways," Life Sciences, Jan. 1, 1993, 52(5-6):521-7.

Basner et al., "Phasic electromyographic activity of the genioglossus increases in normals during slow-wave sleep, " Respir. Physiol., Feb. 1991, 83(2):189-200, 12 pages.

Berry et al., "Acute effects of paroxetine on genioglossus activity in obstructive sleep apnea," Sleep, Dec. 1999, 22(8):1087-1092.

Berry et al., "Rules for scoring respiratory events in sleep: Update of the 2007 aasm manual for the scoring of sleep and associated events. Deliberations of the sleep apnea definitions task force of the American Academy of Sleep Medicine," J. Clin. Sleep Med., Oct. 2012, 8(5):597-619, 23 pages.

Brooks et al., "Obstructive sleep apnea as a cause of systemic hypertension. Evidence from a canine model," J. Clin. Invest., Jan. 1997, 99(1):106-109.

Brownell et al., "Protriptyline in obstructive sleep apnea: a double-blind trial," N. Engl. J. Med., Oct. 1982, 307(17):1037-1042.

Buchanan et al., "5-HT2A receptor activation is necessary for CO2-induced arousal," J Neurophysiol, Jul. 2015, 114(1):233-243, 11 pages.

Carberry et al., "Role of common hypnotics on the phenotypic causes of obstructive sleep apnoea: paradoxical effects of zolpidem," Eur Respir J., 2017, 50:1701344, 11 pages.

Carberry et al., "The effects of zolpidem in obstructive sleep apnea - An open-label pilot study," J Sleep Res, Apr. 2019, 28:e12853, 5 pages.

Carter et al., "Effect of 1 month of zopiclone on obstructive sleep apnoea severity and symptoms: a randomised controlled trial," Eur. Respir. J., Jul. 2018, 52(1):1800149, 12 pages.

Carter et al., "High dose zopiclone does not change osa severity, the respiratory arousal threshold, genioglossus muscle responsiveness or next-day sleepiness and alertness in selected people with OSA," Presented in the form of Abstract at World Sleep 2019, Vancouver, Canada, 2019; Sleep Med., Dec. 2019, 64(Suppl.):S56, 1 page.

Carter et al., "Zopiclone Increases the Arousal Threshold without Impairing Genioglossus Activity in Obstructive Sleep Apnea," Sleep, Apr. 2016, 39(4):757-766, 10 pages.

Chan et al., "Endogenous excitatory drive modulating respiratory muscle activity across sleep-wake states," Am J. Resp Crit Care, Dec. 2006, 174(11):1264-1273.

Clark et al., "Sleep apnea: treatment with protriptyline," Neurology, Sep. 1979, 29(9pt1):1287-1292, 6 pages.

ClinicalTrials.gov [online], "Atomoxetine and Oxybutynin in Obstructive Sleep Apnea (ATOSA)," Sep. 21, 2016, retrieved on Jun. 24, 2020, retrieved from URL<https://clinicaltrials.gov/ct2/show/NCT02908529?term=atomoxetine%2C+oxybutynin&cond=Sleep+Apnea&rank=1>, 7 pages.

CO Office Action in Colombian Appln. No. NC2019/0013180, dated Sep. 24, 2021, 11 pages (with English translation).

Cohn et al., "An update on the use of transdermal oxybutynin in the management of overactive bladder disorder," Ther Adv Urol., Apr. 2016, 8(2):83-90, 8 pages.

Conway et al., "Protriptyline in the treatment of sleep apnoea," Thorax, Jan. 1982, 37(1):49-53, 5 pages.

DrugBank Accession No. DB00245, "Benzatropine, " Jun. 13, 2005, 1 page.

DrugBank Accession No. DB00782, "Propantheline," Jun. 13, 2005, 1 page.

DrugBank Accession No. DB01062, "Oxybutynin," Jun. 13, 2005, 1 page.

DrugBank Accession No. DB08897, "Aclidinium," Jun. 4, 2013, 1 page.

DrugBank Accession No. DB09185, "Viloaxine," Oct. 16, 2015, 1 page.

Eckert et al., "Defining phenotypic causes of obstructive sleep apnea. Identification of novel therapeutic targets," Am. J. Respir. Crit. Care. Med., Oct. 2013, 188(8):996-1004.

(56) References Cited

OTHER PUBLICATIONS

Eckert et al., "Eszopiclone Increases the Respiratory Arousal Threshold and Lowers the apnoea/hypopnoea Index in Obstructive Sleep Apnoea Patients With a Low Arousal Threshold," Clin. Sci. (Lond)., Jun. 2011, 120(12):505-514.

Eckert et al., "Trazodone increases the arousal threshold in obstructive sleep apnea patients with a low arousal threshold," Sleep, Apr. 2014, 37(4):811-819, 9 pages.

Edwards et al., "Acetazolamide improves loop gain but not the other physiological traits causing obstructive sleep apnoea," J. Physiol., Mar. 2012, 590(Pt 5):1199-1211.

Engleman et al., "Improving CPAP use by patients with the sleep apnoea/hypopnoea syndrome (SAHS)," Sleep Med. Rev., Feb. 2003, 7(1):81-99.

EP Extended Search Report in European Appln. No. 18791670.5, dated Jan. 25, 2021, 12 pages.

Fda.gov [online], "FDA approves first generic Strattera for the treatment of ADHD", May 30, 2017, retrieved Sep. 24, 2020 from URL <https://www.fda.gov/news-events/press-announcements/fda-approves-first-generic-strattera-treatment-adhd>, 1 page.

Fenik et al., "REM sleep-like atonia of hypoglossal (XII) motoneurons is caused by loss of noradrenergic and serotonergic inputs," Am. J. Respir. Crit. Care. Med., Nov. 2005, 172(10):1322-1330.

Findley et al., "Automobile accidents involving patients with obstructive sleep apnea," Am. Rev. Respir. Dis., Aug. 1988, 138(2):337-340.

Foldvary-Schaefer et al., "Gabapentin increases slow-wave sleep in normal adults," Epilepsia, Dec. 2002, 43(12):1493-1497, 5 pages.

GE Office Action in Georgian Appln. No. 15226/01, dated May 19, 2020, 3 pages (with English language abstract).

GE Search Report in Georgian Appln. No. 15226/01, dated Dec. 21, 2020, 5 pages (with English summary).

Grace et al., "Identification of the Mechanism Mediating Genioglossus Muscle Suppression in REM Sleep," Am J Respir Crit Care Med, Feb. 2013, 187(3):311-319, 10 pages.

Grace et al., "K+ channel modulation causes genioglossus inhibition in REM sleep and is a strategy for reactivation," Respir. Physiol. Neurobiol., Sep. 2013, 188(3):277-288.

Hanzel et al., "Response of Obstructive Sleep Apnea to Fluoxetine and Protriptyline," Chest, Aug. 1991, 100(2):416-21.

Heinzer et al., "Trazodone increases arousal threshold in obstructive sleep apnoea, " Eur Respir J, Jun. 2008, 31(6):1308-1312, 11 pages.

Hodges et al., "Defects in breathing and thermoregulation in mice with near-complete absence of central serotonin neurons," J. Neurosci., Mar. 2008, 28(10):2495-2505, 11 pages.

Hoffstein, "Blood pressure, snoring, obesity, and nocturnal hypoxaemia, " Lancet, Sep. 1994, 344(8923):643-645.

Horner et al., "State-dependent and reflex drives to the upper airway: basic physiology with clinical implications," J Appl Physiol, Feb. 2014, 116(3):325-336, 13 pages.

Hung et al., "Association of sleep apnoea with myocardial infarction in men," Lancet, Aug. 1990, 336(8710):261-264.

ID Office Action in Indonesian Appln. No. P00201910402, dated Jul. 24, 2021, 7 pages (with English translation).

Kraiczi et al., "Effect of serotonin uptake inhibition on breathing during sleep and daytime symptoms in obstructive sleep apnea," Sleep, Jan. 1999, 22(1):61-67.

Kribbs et al., "Objective measurement of patterns of nasal CPAP use by patients with obstructive sleep apnea," The American Review of Respiratory Disease, Apr. 1993, 147:887-895.

Kubin et al., "Control of Upper Airway Motoneurons During REM Sleep," Apr. 1998, News Physiol. Sci., 13(2):91-97.

Kubin, "Neural Control of the Upper Airway: Respiratory and State-Dependent Mechanisms," Compr Physiol, Sep. 2016, 6(4):1801-1850 50 pages.

Lai et., "Changes in monoamine release in the ventral horn and hypoglossal nucleus linked to pontine inhibition of muscle tone: An in vivo microdialysis study," J Neurosci., 21(8):7384-7391.

Lim et al., "0067 | Reboxetine and hyoscine butylbromide reduce obstructive sleep apnoea severity," Abstract, Presented at Sleep DownUnder 2019 31st ASM of Australasian Sleep Association and the Australasian Sleep Technologists Association, Sydney, Australia, Oct. 16-19, 2019; J. Sleep Res., Oct. 2019, 28(Suppl. 1): p. 31, 1 page.

Lim et al., "Reboxetine and hyoscine butylbromide improve upper airway function during nonrapid eye movement and suppress rapid eye movement sleep in healthy individuals," Sleep, Apr. 2019, 42(4):zsy261, 10 pages.

Marshall et al., "Two Randomized Placebo-Controlled Trials to Evaluate the Efficacy and Tolerability of Mirtazapine for the Treatment of Obstructive Sleep Apnea, " Sleep, Jun. 2008, 31(6):824-831.

Matthews et al., "Selective noradrenaline reuptake inhibitors for schizophrenia," Cochrane Database of Systematic Reviews, Jan. 2018, (1), 129 pages.

Nicholas et al., "Discharge patterns of human tensor palatini motor units during sleep onset," Sleep, May 2012, 35(5):699-707, 9 pages.

Nieto et al., "Association of sleep-disordered breathing, sleep apnea, and hypertension in a large community-based study," Sleep heart health study, JAMA, Apr. 2000, 283(14):1829-1836, 9 pages.

PCT International Preliminary Report on Patentability in International Appln. PCT/US2018/029518, dated Oct. 29, 2019, 10 pages.

PCT International Preliminary Report on Patentability in International Appln. PCT/US2020/017323, dated Aug. 10, 2021, 8 pages.

PCT International Search Report and Written Opinion in international application No. PCT/US2018/029518, dated Aug. 21, 2018, 16 pages.

PCT International Search Report and Written Opinion in international application No. PCT/US2020/017323, dated Jun. 26, 2020, 12 pages.

Peppard et al., "Increased Prevalence of Sleep-Disordered Breathing in Adults," Am. J. Epidemiol., May 2013, 177(9):1006-1014.

Peppard et al., "Prospective study of the association between sleep-disordered breathing and hypertension," The New England Journal of Medicine, May 2000, 342(19):1378-1384, 9 pages.

Rao et al., "Gabapentin augments whole blood serotonin in healthy young men," J Neural Transm., 1988, 73(2):129-134, 6 pages.

Ratnavadivel et al., "Marked reduction in obstructive sleep apnea severity in slow wave sleep," J Clin Sleep Med., Dec. 2009, 5(6):519-524, 6 pages.

Redline et al., "Neuropsychological function in mild sleep-disordered breathing," Sleep, Feb. 1997, 20(2):160-167.

Ruehland et al., "The new AASM criteria for scoring hypopneas: Impact on the apnea hypopnea index," Sleep, Feb. 2009, 32(2):150-157, 9 pages.

Sands et al., "Enhanced Upper-Airway Muscle Responsiveness Is a Distinct Feature of Overweight/Obese Individuals without Sleep Apnea," Am J Respir Crit Care Med., Oct. 2014, 190(8):930-937, 8 pages.

Sands et al., "Phenotyping pharyngeal pathophysiology using polysomnography in patients with obstructive sleep apnea, " Am J Respir Crit Care Med, May 2018, 197(9):1187-1197, 11 pages.

Sands et al., "Quantifying the arousal threshold using polysomnography in obstructive sleep apnea," Sleep, Jan. 2018, 41(1):zsx183, 9 pages.

Sangal et al., "Atomoxetine Improves Sleepiness and Global Severity of Illness but Not the Respiratory Disturbance Index in Mild to Moderate Obstructive Sleep Apnea With Sleepiness," Sleep Med., Jul. 2008, 9(5):506-510.

Shahar et al., "Sleep-disordered breathing and cardiovascular disease: Cross-sectional results of the sleep heart health study," Am. J. Respir. Crit. Care Med., Jan. 2001, 163(1):19-25.

Smales et al., "Trazodone Effects on Obstructive Sleep Apnea and Non-REM Arousal Threshold," Ann Am Thorac Soc, May 2015, 12(5):758-764, 7 pages.

Smith et al., "The effects of protriptyline in sleep-disordered breathing," Am Rev Respir Dis, 1983; 127(1):8-13, 6 pages.

Somers et al., "Sympathetic neural mechanisms in obstructive sleep apnea," J. Clin. Invest., Oct. 1995, 96(4):1897-1904.

Song et al., "Alpha2-adrenergic blockade rescues hypoglossal motor defense against obstructive sleep apnea," JCI Insight, Feb. 2017, 2:e91456, 16 pages.

(56) References Cited

OTHER PUBLICATIONS

Sood et al., "Genioglossus muscle activity and serotonergic modulation of hypoglossal motor output in obese Zucker rats," J. Appl. Physiol., Jun. 2007, 102(6):2240-2250.

Sood et al., "Inhibition of serotonergic medullary raphe obscurus neurons suppresses genioglossus and diaphragm activities in anesthetized but not conscious rats," J. Appl. Physiol., Jun. 2006, 100:1807-1821.

Sood et al., "Role of endogenous serotonin in modulating genioglossus muscle activity in awake and sleeping rats," American Journal of Respiratory and Critical Care Medicine, Nov. 2005, 172(10):1338-1347.

Taranto-Montemurro et al., "Desipramine improves upper airway collapsibility and reduces OSA severity in patients with minimal muscle compensation," Eur Respir J, Oct. 2016, 48:1340-1350, 11 pages.

Taranto-Montemurro et al., "Effects of Tiagabine on Slow Wave Sleep and Arousal Threshold in Patients With Obstructive Sleep Apnea," Sleep, Feb. 2017, 40(2):zsw047, 7 pages.

Taranto-Montemurro et al., "Neural memory of the genioglossus muscle during sleep is stage- dependent in healthy subjects and obstructive sleep apnoea patients," The Journal of physiology, Jul. 2018, 596(21):5163-5173, 11 pages.

Taranto-Montemurro et al., "Targeting Endotypic Traits with Medications for the Pharmacological Treatment of Obstructive Sleep Apnea. A Review of the Current Literature," J Clin Med, Nov. 2019, 8(11):1846, 26 pages.

Taranto-Montemurro et al., "The Combination of Atomoxetine and Oxybutynin Greatly Reduces Obstructive Sleep Apnea Severity," American Journal of Respiratory and Critical Care Medicine, May 2019, 199(10):1267-1276.

Taranto-Montemurro et al., "Desipramine Increases Genioglossus Activity and Reduces Upper Airway Collapsibility during Non-REM Sleep in Healthy Subjects," American Journal of Respiratory and Critical Care Medicine 194(7), 36 pages.

Thornton, "Sleep aids and sedatives," JACEP, Sep. 1977, 6(9):408-412, 5 pages.

Weaver & Gurnstein., "Adherence to Continuous Positive Airway Pressure Therapy: The Challenge to Effective Treatment," Proc. Am. Thorac. Soc., Feb. 2008, 5(2):173-178.

Weerts et al., "Restricted sedation and absence of cognitive impairments after administration of intranasal scopolamine," J Psychopharmacol, Aug. 2015, 29(12):1231-1235, 5 pages.

Weiner et al., "5-Hydroxytryptamine2A Receptor Inverse Agonists as Antipsychotics," The Journal of Pharmacology and Experimental Therapeutics, Oct. 2001, 299(1):268-276, 9 pages.

Wellman et al., "A method for measuring and modeling the physiological traits causing obstructive sleep apnea," J. Appl. Physiol., Jun. 2011, 110(6):1627-1637, 12 pages.

Wellman et al., "A simplified method for determining phenotypic traits in patients with obstructive sleep apnea," J. Appl. Physiol., Apr. 2013, 114(7):911-922.

Wellman et al., "Effect of oxygen in obstructive sleep apnea: Role of loop gain," Respir. Physiol. Neurobiol., Jul. 2008, 162(2):144-151, 9 pages.

Wessendorf et al., "Sleep-disordered breathing among patients with first-ever stroke," J. Neurol., Jan. 2000, 247(1):41-47.

White et al., "The antagonisms of atropine to the eeg effects of adrenergic drugs," J Pharmacol Exp Ther., Apr. 1959, 125(4):339-346, 8 pages.

Whyte et al., "Role of protriptyline and acetazolamide in the sleep apnea/hypopnea syndrome," Sleep, Oct. 1988, 11(5):463-472, 10 pages.

Wilkinson et al., "Discharge patterns of human genioglossus motor units during sleep onset," Sleep, Apr. 2008, 31(4):525-533, 9 pages.

Yokoyama et al., "Once-daily oxybutynin patch improves nocturia and sleep quality in Japanese patients with overactive bladder: Post-hoc analysis of a phase III randomized clinical trial," Int J Urol, Mar. 2015, 22:684-688, 5 pages.

Younes, "Contributions of upper airway mechanics and control mechanisms to severity of obstructive apnea," Am. J. Respir. Crit. Care Med., Sep. 2003, 168(6):645-658.

Young et al., "Burden of Sleep Apnea: Rationale, Design, and Major Findings of the Wisconsin Sleep Cohort Study," WMJ, Aug. 2009, 108(5):246-249, 8 pages.

Young et al., "Epidemiology of obstructive sleep apnea: a population health perspective," Am. J. Respir. Crit. Care. Med., May 2002;, 165(9):1217-1239.

AU Office Action in Australian Appln. No. 2018260666, dated May 5, 2022, 4 pages.

MX Office Action in Mexican Appln. No. MX/a/2019/012729, dated Mar. 14, 2022, 6 pages (with English translation).

IL Office Action in Israeli Appln. No. 270204, dated Apr. 7, 2022, 12 pages (English translation).

JP Japanese Office Action in Japanese Appln. No. 2019-558554, dated May 17, 2022, 10 pages (with English translation).

AU Office Action in Australian Appln. No. 2020219809, mailed on Sep. 20, 2024, 5 pages.

AU Office Action in Australian Appln. No. 2022241471, mailed on Sep. 18, 2024, 4 pages.

BR Office Action in European Appln. No. 1120210156003, mailed on Aug. 16, 2024, 5 pages (with English translation).

ID Office Action in Indonesian Appln. No. P00202106608, mailed on Oct. 10, 2024, 6 pages (with English translation).

IL Office Action in Israeli Appln. No. 270204, mailed on Aug. 21, 2024, 5 pages (English translation).

JP Office Action in Japanese Appln. No. 2023-108387, mailed on Jul. 30, 2024, 8 pages (with English translation).

Mansfield, "Role of fesoterodine in the treatment of overactive bladder," Open Access Journal of Urology, Dec. 2009, 1-9.

Umlauf et al., "Obstructive sleep apnea, nocturia and polyuria in older adults," Sleep, Feb. 2004, 27(1):139-44.

EA Office Action in Eurasian Appln. No. 201992569, dated Nov. 7, 2022, 5 pages (with English translation).

VN Office Action in Vietnamese Appln. No. 1-2019-06672, dated Oct. 12, 2022, 5 pages (with English translation).

IN Office Action in Indian Appln. No. 202117035557, dated Feb. 20, 2023, 9 pages.

JP Japanese Office Action in Japanese Appln. No. 2019-558554, dated Feb. 28, 2023, 11 pages (with English translation).

CO Office Action in Colombian Appln. No. NC2022/0016839, dated Apr. 14, 2023, 15 pages (with English summary).

IL Office Action in Israeli Appln. No. 270204, mailed on Jul. 6, 2023, 7 pages (English translation).

MX Office Action in Mexican Appln. No. MX/a/2022/010349, dated Mar. 9, 2023, 5 pages (with English translation).

PH Office Action in Filipino Appln. No. 2019502427, mailed on Sep. 11, 2023, 6 pages.

SV Office Action in Salvadoran Appln. No. 2019005979, mailed on Jul. 10, 2023, 9 pages (with English translation).

CN Office Action in Chinese Appln. No. 201880042623.1, dated Aug. 3, 2022 , 19 pages (with English translation).

DO Office Action in Dominican Appln. No. P2019-0274, dated Jul. 4, 2022, 8 pages (with English translation).

EC Office Action in Ecuadorian Appln. No. 2019-84058, dated Jul. 22, 2022, 25 pages (with English translation).

EP Extended Search Report in European Appln. No. 20752195.6, dated Oct. 10, 2022, 8 pages.

SV Office Action in Salvadorian Appln. No. 2019005979, dated Jun. 14, 2022, 11 pages (with English translation).

UA Office Action in Ukrainian Appln. No. a 2019 10615, dated Sep. 2, 2022, 8 pages (with English translation).

CN Office Action in Chinese Appln. No. 202080026282.6, dated May 31, 2023, 13 pages (with English translation).

EA Office Action in Eurasian Appln. No. 202192202, mailed on Sep. 1, 2023, 6 pages (with English translation).

Griebel et al., "Further evidence for the sleep-promoting effects of 5-HT2A receptor antagonists and demonstration of synergistic effects with the hypnotic, zolpidem in rats," Neuropharmacology, Jul. 1, 2013, 70:19-26.

KR Office Action in Korean Appln. No. 1020197034523, dated May 19, 2023, 16 pages (with English translation).

(56) References Cited

OTHER PUBLICATIONS

NZ Office Action in New Zealand Appln. No. 758564, dated Jul. 6, 2023, 4 pages.

Sullivan et al., "Emerging drugs for common conditions of sleepiness: obstructive sleep apnea and narcolepsy," Expert Opinion on Emerging Drugs, Oct. 2, 2015, 20(4):571-82.

SV Office Action in Salvadorian Appln. No. 2019005979, dated Apr. 27, 2023, 9 pages (with English translation).

EA Office Action in Eurasian Appln. No. 201992569/28, dated Feb. 10, 2022, 10 pages (with English translation).

UA Office Action in Ukrainian Appln. No. 2019-10615, dated Mar. 29, 2022, 7 pages (with English translation).

CA Office Action in Canadian Appln. No. 3,061,468, mailed on May 23, 2024, 3 pages.

CN Office Action in Chinese Appln. No. 201880042623.1, mailed on Jul. 6, 2024, 12 pages (with English translation).

CN Office Action in Chinese Appln. No. 202080026282.6, mailed on Jan. 30, 2024, 14 pages (with English translation).

CO Office Action in Colombian Appln. No. NC2022/0016839, mailed on Mar. 14, 2024, 24 pages (with English translation).

CR Office Action in Costa Rican Appln. No. 2019-0546, mailed on Mar. 18, 2024, 16 pages (with English translation).

Cummings et al., "Alzheimer's disease drug development pipeline: 2018," Alzheimer's & Dementia: Translational Research & Clinical Interventions, Jan. 2018, 4:195-214.

EA Office Action in Eurasian Appln. No. 202392997, mailed on May 23, 2024, 8 pages (with English translation).

EG Office action in Egyptian Appln. No. 1692/2019, mailed on Mar. 5, 2024, 12 pages (with English translation).

EP Office Action in European Appln. No. 18791670.5, mailed on Mar. 25, 2024, 8 pages.

GE Office Action in Georgian Appln. No. 16320/1, mailed on Jan. 18, 2024, 9 pages (with English translation).

IL Office Action in Israeli Appln. No. 285197, mailed on Mar. 26, 2024 (with English translation).

JP Office Action in Japanese Appln. No. 2021-546285, mailed on Jan. 23, 2024, pages (with English translation).

KR Office Action in Korean Appln. No. 10-2024-7009759, mailed on Apr. 29, 2024, 8 pages (with English translation).

Martin et al., "Effect of ipratropium bromide treatment on oxygen saturation and sleep quality in COPD," Chest, May 1999, 115(5):1338-45.

MX Office Action in Mexican Appln. No. MX/a/2021/009407, mailed on May 2, 2024, 10 pages (with English translation).

MX Office Action in Mexican Appln. No. MX/a/2022/010349, mailed on Feb. 8, 2024, 10 pages (with English translation).

PH Office Action in Filipino Appln. No. 2019502427, mailed on May 27, 2024, 4 pages.

Rae et al., "Atomoxetine restores the response inhibition network in Parkinson's disease, " Brain, Aug. 2016, 139(8):2235-48.

SG Office Action in Singaporean Appln. No. 11202108225Q, mailed on Jun. 6, 2024, 7 pages.

VN Office Action in Vietnamese Appln. 1-2021-05223, mailed on Feb. 27, 2024, 4 pages (with English translation).

VN Office Action in Vietnamese Appln. No. 1-2019-06672, mailed on Apr. 16, 2024, 4 pages (with English translation).

Wang et al., "Drug effects on ventilatory control and upper airway physiology related to sleep apnea," Respiratory Physiology & Neurobiology, Sep. 2013, 188(3):257-66.

EA Office Action in Eurasian Appln. No. 202392997, mailed on Dec. 7, 2023, 4 pages (with English translation).

EP Office Action in European Appln. No. 20752195.6, mailed on Nov. 24, 2023, 4 pages.

KR Office Action in Korean Appln. No. 10-2019-7034523, mailed on Nov. 21, 2023, 7 pages (with English translation).

BR Office Action in Brazilian Appln. No. BR112019022483-1, dated May 31, 2022, 7 pages (with English translation).

CO Office Action in Colombian Appln. No. NC2019/0013180, May 13, 2022, 9 pages (with English translation).

IN Office Action in Indian Appln. No. 202118059526, dated May 24, 2022, 6 pages (with English translation).

CA Office Action in Canadian Appln. No. 3,129,270, mailed on Feb. 6, 2025, 4 pages.

Hacksell et al., "On the discovery and development of pimavanserin: a novel drug candidate for Parkinson's psychosis," Neurochemical Research, Oct. 2014, 39:2008-17.

ID Office Action in Indonesian Appln. No. P00201910402, mailed on Dec. 30, 2024, 2 pages.

Meltzer et al., "Pimavanserin, a selective serotonin (5-HT) 2A-inverse agonist, enhances the efficacy and safety of risperidone, 2 mg/day, but does not enhance efficacy of haloperidol, 2 mg/day: comparison with reference dose risperidone, 6 mg/day," Schizophrenia Research, Nov. 2012, 141(2-3):144-52.

MX Office Action in Mexican Appln. No. MX/a/2021/009407, mailed on Feb. 4, 2025, 9 pages (with English translation).

MY Office Action in Malaysian Appln. No. PI2021004502, mailed on Mar. 14, 2025.

Price et al., "Cunningham KA. Pimavanserin and lorcaserin attenuate measures of binge eating in male Sprague-Dawley rats," Frontiers in Pharmacology, Dec. 2018, 9:1424.

EA Search Report in Eurasian Appln. No. 202492243, mailed on Apr. 10, 2025, 4 pages (with English translation).

CO Office Action in Colombian Appln. No. NC2022/0016839, mailed on Sep. 18, 2024, 10 pages (with English translation).

KR Office Action in Korean Appln. No. 10-2024-7009759, mailed on Nov. 21, 2024, 8 pages (with English translation).

UA Office Action in Ukrainian Appln. No. 2021-04441, mailed on Nov. 13, 2024, 11 pages (with English translation).

BR Office Action in Brazilian Appln. No. BR112019022483-1, mailed on Jun. 10, 2025, 8 pages (with English translation).

Diefenbach et al., "Randomised, double-blind study of the effects of oxybutynin, tolterodine, trospium chloride and placebo on sleep in healthy young volunteers," Clinical Drug Investigation, Jun. 2003, 23:395-404.

EA Eurasian Office Action in Eurasian Appln. No. 202392997, mailed on Apr. 1, 2025, 8 pages (with English translation).

EA Office Action in Eurasian Appln. No. 202492243, mailed on May 6, 2025, 10 pages (with English translation).

ID Indonesian Office Action in Indonesian Appln. No. P00201910402, mailed on Apr. 22, 2025, 5 pages (with English translation).

IL Office Action in Israeli Appln. No. 285197, mailed on Apr. 21, 2025, 5 pages (English translation).

KR Office Action in Korean Appln. No. 10-2021-7027063, mailed on May 28, 2025, 20 pages (with English translation).

KR Office Action in Korean Appln. No. 10-2024-7009759, mailed on Aug. 10, 2025, 8 pages (with English translation).

NZ Office Action in New Zealand Appln. No. 798875, mailed on Apr. 30, 2025, 4 pages.

* cited by examiner

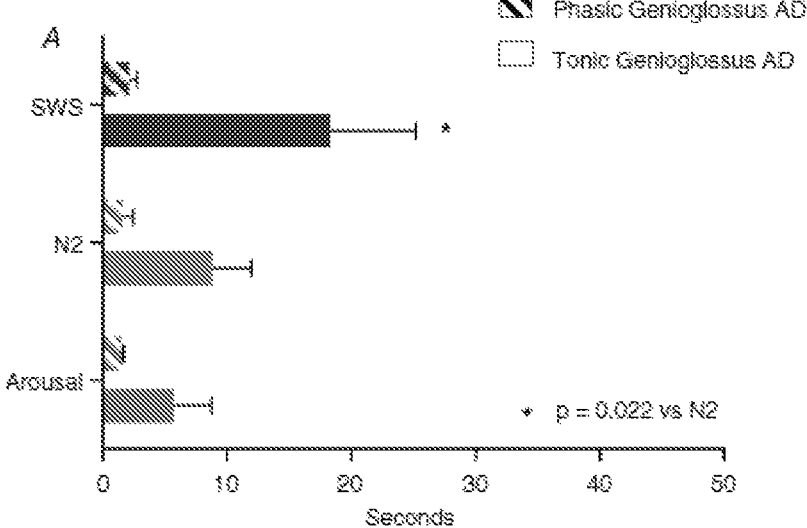
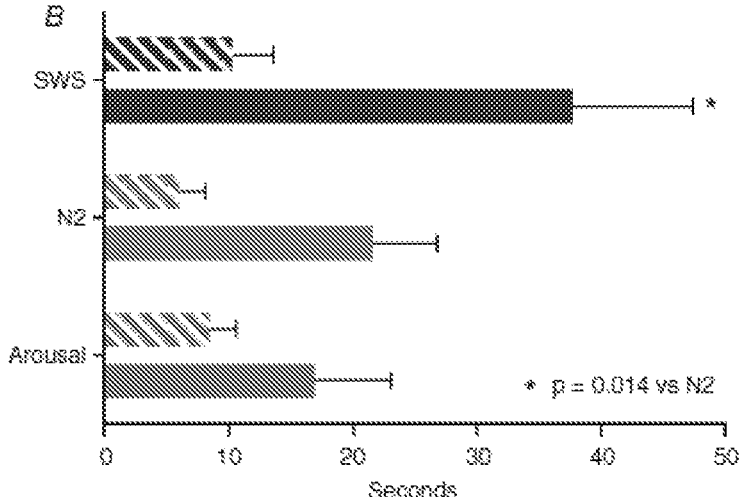
*FIGs. 5A-B*

METHODS AND COMPOSITIONS FOR TREATING SLEEP APNEA

CLAIM OF PRIORITY

This application claims the benefit of U.S. Provisional Patent Application Ser. No. 62/803,223, filed on Feb. 8, 2019. The entire contents of the foregoing are hereby incorporated by reference.

FEDERALLY SPONSORED RESEARCH OR DEVELOPMENT

This invention was made with Government support under Grant Nos. HL102321 and HL095491 awarded by the National Institutes of Health. The Government has certain rights in the invention.

TECHNICAL FIELD

The present invention is based, at least in part, on the discovery of methods and compositions for the treatment of conditions associated with pharyngeal airway collapse while the subject is in a non-fully conscious state, e.g., snoring and sleep apnea, comprising administration of a norepinephrine reuptake inhibitor (NRI) and a non myorelaxing hypnotic or 5-HT2A inverse agonist or antagonist.

BACKGROUND

Obstructive Sleep Apnea (OSA) is a common disorder (Young et al., Am J Respir Crit Care Med 2002; 165:1217-39) caused by collapse of the pharyngeal airway during sleep. OSA can have serious health consequences.

SUMMARY

The present disclosure is based upon the administration of noradrenergic and non-myorelaxing hypnotic drugs to increase pharyngeal muscle activity in sleeping humans and reduce snoring and sleep apnea severity, e.g., in OSA patients.

Thus, provided herein are methods for treating a subject having a condition associated with pharyngeal airway collapse while the subject is in a non-fully conscious state. The methods include administering to a subject in need thereof an effective amount of (i) a norepinephrine reuptake inhibitor (NRI) and (ii) a non myorelaxing hypnotic and/or 5-HT2A inverse agonist or antagonist.

In some embodiments, the NRI is a norepinephrine selective reuptake inhibitor (NSRI), e.g., an NSRI selected from the group consisting of Amedalin, Atomoxetine, CP-39,332, Daledalin, Edivoxetine, Esreboxetine, Lortalamine, Nisoxetine, Reboxetine, Talopram, Talsupram, Tandamine, and Viloxazine.

In some embodiments, the NRI is a norepinephrine non-selective reuptake inhibitor (NNRI), e.g., an NNRI selected from the group consisting of Amitriptiline, Amoxapine, Bupropion, Ciclazindol, Desipramine, Desvenlafaxine, Dexmethilphenidate, Diethylpropion, Doxepin, Duloxetine, Imipramine, Levomilnacipran, Manifaxine, Maprotiline, Methylphenidate, Milnacipran, Nefazodone, Nortriptyline, Phendimetrazine, Phenmetrazine, Protryptyline, Radafaxine, Tapentadol, Teniloxazine, and Venlafaxine.

In some embodiments, the NRI is selected from the group consisting of Atomoxetine and Reboxetine.

In some embodiments, the NRI is Atomoxetine, and in specific embodiments, the dosage of Atomoxetine is 20-100 mg, e.g., 25-75 mg.

In some embodiments, the non myorelaxing hypnotic is a benzodiazepine hypnotic, e.g., temazepam, brotizolam, flurazepam, nitrazepam, or triazolam; or a non-benzodiazepine hypnotic, e.g., a cyclopyrrolone hypnotic, e.g., zolpidem, zopiclone or eszopiclone, a stereoisomer of zopiclone; gabapentin; trazodone; diphenhydramine; suvorexant; tasimelteon; ramelteon; agomelatine; doxepin; zaleplon; doxylamine; sodium oxybate; or tiagabine.

In some embodiments, the 5-HT2A inverse agonist is AC-90179, ketanserin, nelotanserin, eplivanserin, pimavanserin, or volinanserin; or the 5-HT2A antagonist is trazodone, mirtazapine, ketanserin, clozapine, olanzapine, quetiapine, risperidone, iloperidone, perospirone, asenapine, nefazodone, MDL-100,907, cyproheptadine, pizotifen, LY-367,265, 2-alkyl-4-aryl-tetrahydro-pyrimido-azepines, haloperidol, chlorpromazine, hydroxyzine (Atarax), 5-MeO-NBpBrT, or Niaprazine. In some embodiments, the 5-HT2A antagonist is ketanserin, iloperidone, perospirone, risperdone or nefazodone.

In some embodiments, the 5-HT2A inverse agonist or antagonist is pimvanserin, preferably administered at a dose of 20-40 mg, preferably 34 mg.

In some embodiments, the non myorelaxing hypnotic or 5-HT2A inverse agonist or antagonist is in an immediate release formulation.

In some embodiments, the non myorelaxing hypnotic or 5-HT2A inverse agonist or antagonist is in an extended release formulation.

In some embodiments, the non myorelaxing hypnotic is zolpidem, and in specific embodiments, the dosage of zolpidem is 2-12.5 mg.

In some embodiments, the zolpidem is in an immediate release formulation, e.g., with a dose of 2-10 mg.

In some embodiments, the zolpidem is in an extended release formulation, e.g., with a dose of 5-12.5 mg.

In some embodiments, the disease or disorder is Obstructive Sleep Apnea (e.g., AHI of ≥10 events per hour) or Simple Snoring.

In some embodiments, the non-fully conscious state is sleep.

In some embodiments, the NRI and the non myorelaxing hypnotic are administered in a single composition.

In some embodiments, the NRI and 5-HT2A inverse agonist or antagonist are administered in a single composition.

In some embodiments, the single composition is an oral administration form.

In some embodiments, the oral administration form is a syrup, pill, tablet, troche, or capsule.

In some embodiments, the single composition is a transdermal administration form, e.g., a patch.

Also provided herein are pharmaceutical compositions comprising (i) a norepinephrine reuptake inhibitor (NRI) (ii) a non myorelaxing hypnotic and/or 5-HT2A inverse agonist or antagonist, and (iii) a pharmaceutically acceptable carrier.

In some embodiments, the NRI is a norepinephrine selective reuptake inhibitor (NSRI), e.g., selected from the group consisting of Amedalin, Atomoxetine, CP-39,332, Daledalin, Edivoxetine, Esreboxetine, Lortalamine, Nisoxetine, Reboxetine, Talopram, Talsupram, Tandamine, and Viloxazine. In some embodiments, the NRI is a norepinephrine non-selective reuptake inhibitor (NNRI) selected from the group consisting of Amitriptiline, Amoxapine, Bupropion, Ciclazindol, Desipramine, Desvenlafaxine, Dexme-

3 thilphenidate, Diethylpropion, Doxepin, Duloxetine, Imipramine, Levomilnacipran, Manifaxine, Maprotiline, Methylphenidate, Milnacipran, Nefazodone, Nortriptyline, Phendimetrazine, Phenmetrazine, Protryptyline, Radafaxine, Tapentadol (Nucynta), Teniloxazine (Lucelan, Metatone) and Venlafaxine.

In some embodiments, the NRI is selected from the group consisting of Atomoxetine and Reboxetine.

In some embodiments, the NRI is Atomoxetine, and in specific embodiments, the dosage of Atomoxetine is 20-100 mg.

In some embodiments, the non myorelaxing hypnotic is a benzodiazepine hypnotic, e.g., temazepam, brotizolam, flurazepam, nitrazepam, or triazolam; or a non-benzodiazepine hypnotic, e.g., a cyclopyrrolone hypnotic, preferably selected from the group consisting of zolpidem, zopiclone, and eszopiclone; gabapentin; trazodone; diphenhydramine; suvorexant; tasimelteon; ramelteon; agomelatine; doxepin; zaleplon; doxylamine; sodium oxybate; or tiagabine, In some embodiments, the non myorelaxing hypnotic is in an immediate release formulation. In some embodiments, the non myorelaxing hypnotic is in an extended release formulation.

In some embodiments, the non myorelaxing hypnotic is zolpidem. In some embodiments, the zolpidem is in an immediate release formulation, e.g., with a dose of 2-10 mg. In some embodiments, the zolpidem is in an extended release formulation, e.g., with a dose of 5-12.5 mg.

In some embodiments, the 5-HT2A inverse agonist is AC-90179, ketanserin, nelotanserin, eplivanserin, pimavanserin, or volinanserin; or the 5-HT2A antagonist is trazodone, mirtazapine, ketanserin, clozapine, olanzapine, quetiapine, risperidone, iloperidone, perospirone, asenapine, nefazodone, MDL-100,907, cyproheptadine, pizotifen, LY-367,265, 2-alkyl-4-aryl-tetrahydro-pyrimido-azepines, haloperidol, chlorpromazine, hydroxyzine (Atarax), 5-MeO-NBpBrT, or Niaprazine. In some embodiments, the 5-HT2A antagonist is ketanserin, iloperidone, perospirone, risperidone or nefazodone.

In some embodiments, the 5-HT2A inverse agonist or antagonist is pimvanserin, present in a dose of 20-40 mg or 30-40 mg, preferably 34 mg.

Also provided are the compositions described herein for use in treating a subject having a condition associated with pharyngeal airway collapse while the subject is in a non-fully conscious state. In some embodiments, the disease or disorder is sleep apnea or Simple Snoring. In some embodiments, the disease or disorder is Obstructive Sleep Apnea.

In some embodiments, the non-fully conscious state is sleep.

In some embodiments, the NRI and the non myorelaxing hypnotic are administered in a single composition.

In some embodiments, the single composition is an oral administration form.

In some embodiments, the oral administration form is a pill, tablet, troche, or capsule.

Also provided herein are a norepinephrine reuptake inhibitor (NRI) and a non myorelaxing hypnotic and/or 5-HT2A inverse agonist or antagonist, for use in treating a subject having a condition associated with pharyngeal airway collapse while the subject is in a non-fully conscious state.

Further, provided herein are kits comprising (i) a norepinephrine reuptake inhibitor (NRI) and (ii) a non myorelaxing hypnotic and/or 5-HT2A inverse agonist or antagonist, e.g., for use in method described herein, e.g., for treating a subject having a condition associated with pharyngeal airway collapse while the subject is in a non-fully conscious state. The kit can comprise, e.g., separate pharmaceutical compositions of any of the individual active drugs claimed herein with a pharmaceutically acceptable salt or carrier wherein said kit may contain (a) separate or common bottles or packets allowing potentially separate dosaging and (b) optionally a set of kit instructions.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 5A-B. After inducing a reflex activation of the genioglossus muscle with a transient obstruction of the upper airway during sleep, the time during which the activity of the genioglossus remained elevated above baseline after the obstructive stimulus was removed was 2-fold longer during slow wave sleep (SWS) compared to NREM 2 (N2) sleep.

DETAILED DESCRIPTION

Figure 1:
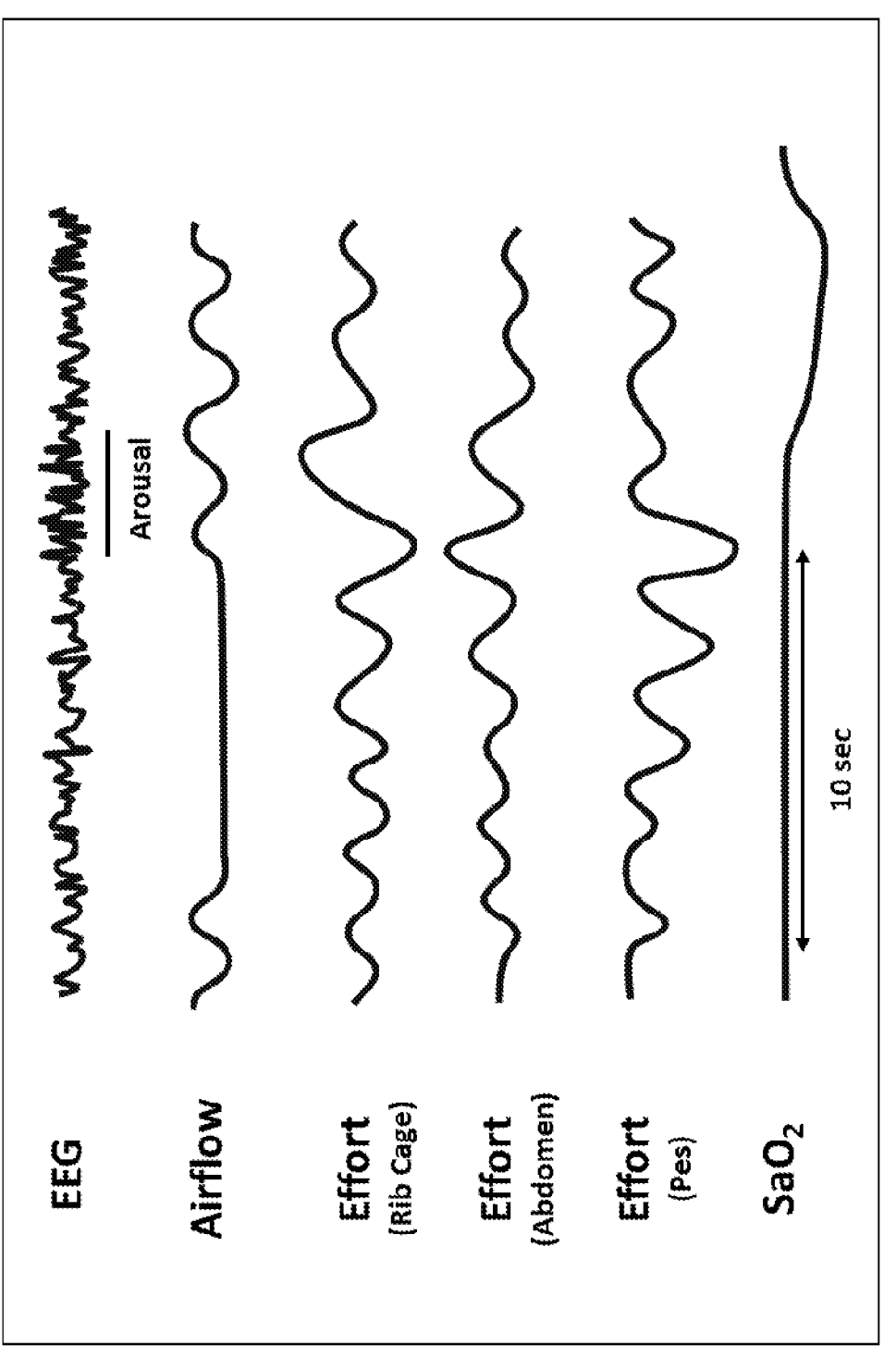
FIG. 1. Graphic illustration of an obstructive apnea. The top channel shows the electroencephalogram (EEG) pattern of sleep. The next channel represents airflow. The next three channels show ventilatory effort by movements of the rib cage and abdomen and changes in esophageal pressure, all of which reflect contraction of respiratory muscles. The last channel indicates oxyhemoglobin saturation.

In humans, the pharyngeal airway region has no bone or cartilage support, and it is held open by muscles. When these muscles relax during sleep, the pharynx can collapse resulting in cessation of airflow. As shown in FIG. 1, ventilatory effort continues and increases in an attempt to overcome the obstruction, shown by an increase in the amplitude of esophageal pressure swings. Rib cage and abdominal movements are in the opposite direction as a result of the diaphragm contracting against an occluded airway, forcing the abdominal wall to distend out and the chest wall to cave inward.

Increasing efforts to breathe lead to an arousal from sleep, visualizable on an EEG (FIG. 1), and result in opening of the airway and a resumption of normal breathing. The lack of airflow during the apnea also causes hypoxia, shown by a drop in oxyhemoglobin saturation (FIG. 1). Severity is generally measured using the apnea-hypopnea index (AHI), which is the combined average number of apneas (cessation of breathing for at least ten seconds) and hypopneas (reduced airflow and oxygen saturation) that occur per hour of sleep. See, for example, Ruehland et al., The new AASM criteria for scoring hypopneas: Impact on the apnea hypopnea index. SLEEP 2009; 32 (2):150-157.

When a stringent definition of OSA is used (an AHI of ≥15 events per hour or AHI≥5 events per hour with daytime sleepiness), the estimated prevalence is approximately 15 percent in males and 5 percent in females. An estimated 30 million individuals in the United States have OSA, of which approximately 6 million have been diagnosed. The prevalence of OSA in the United States appears to be increasing due to aging and increasing rates of obesity. OSA is associated with major comorbidities and economic costs, including: hypertension, diabetes, cardiovascular disease, motor vehicle accidents, workplace accidents, and fatigue/lost productivity. See, for example, Young et al., WMJ 2009; 108:246; Peppard et al., Am J Epidemiol 2013; 177:1006.

The present leading treatment (Engleman and Wild, Sleep Med Rev 2003; 7:81-99; Kribbs et al., The American review of respiratory disease 1993; 147:887-95) is continuous positive airway pressure (CPAP). CPAP is effective in virtually all patients, and approximately 85% of diagnosed patients are treated, but compliance is low. Patients find CPAP uncomfortable and often intolerable; at least 30% of patients (up to 80%) are regularly non-adherent and thus untreated (Weaver, Proc Am Thorac Soc. 2008 Feb. 15; 5(2): 173-178). Other treatment modalities with variable rates of success include oral appliances (10%) and surgery (5%), but neither is likely to be effective across the general population. No pharmacologic treatments have been shown to be effective to date.

The search for medicines to activate pharyngeal muscles in sleeping humans has been discouraging; agents such as serotonin reuptake inhibitors, tricyclic antidepressants, and sedatives have all been tested in humans and shown to be ineffective at reducing OSA severity. When taken alone, noradrenergic drugs such as norepinephrine reuptake inhibitors only mildly reduce OSA severity, and only in selected patients. See, e.g., Proia and Hudgel, Chest. 1991 August; 100 (2):416-21; Brownell et al., N Engl J Med 1982, 307: 1037-1042; Sangal et al., Sleep Med. 2008 Jul. 9 (5):506-10. Epub 2007 Sep. 27; Marshall et al., Sleep. 2008 June; 31 (6):824-31; Eckert et al., Clin Sci (Lond). 2011 June; 120 (12):505-14; Taranto-Montemurro et al., Sleep. 2017 Feb. 1; 40(2).

The tricyclic antidepressants protriptyline (Brownell et al. N Engl J Med 1982; 307:1037-1042; Smith et al. Am Rev Respir Dis 1983; 127:8-139) and desipramine (Taranto-Montemurro et al. Eur Respir J 2016; 48:1340-135), as well as the selective norepinephrine reuptake inhibitor atomoxetine (Bart Sangal et al. Sleep Med 2008; 9:506-510), have all been tested in patients with OSA, with modest success in reducing the severity of the disorder. Three randomized controlled trials (Brownell et al. 1982, supra; Whyte et al. Sleep 1988; 11:463-472; Hanzel et al. Chest 1991; 100:416-421) and several observational studies (Smith et al. supra; Conway et al. Thorax 1982; 37:49-53; Clark et al. Neurology 1979; 29:1287-1292) assessed the effects of protriptyline on OSA severity. Brownell and co-workers (Brownell et al. 1982, supra) found no change in AHI during NREM sleep after 4 weeks of therapy with protriptyline 20 mg in a group of 5 obese men with severe OSA. However, the patients had improvements in oxygen saturation and daytime sleepiness, suggesting at least some positive impact of the drug on respiration during sleep. In another double-blind trial, Whyte and coworkers (Whyte et al. 1988, supra) found that administration of protriptyline 20 mg for 14 days in 10 moderate-to-severe OSA patients did not change NREM AHI as a group, but the inter-individual variability in response was substantial. Lastly, in an open label, 4-week crossover trial on 9 patients, Hanzel et al (Chest 1991; 100:416-421) showed a statistically significant reduction in AHI by 42% from baseline. These results, taken together, suggest that protriptyline may be helpful in a subgroup of OSA patients that still needs to be identified.

Similar to protriptyline, another tricyclic drug, desipramine, was tested in a placebo-controlled, double blind crossover trial lasting 1 night. However, variable results were obtained in terms of AHI reduction in the 14 patients studied (Taranto-Montemurro et al. 2016, supra). Although the effect on OSA severity was not significant as a group, patients exhibited a less collapsible airway on desipramine compared to placebo. Moreover, a post-hoc analysis identified the subgroup of patients with minimal muscle compensation as the phenotype that responded best to the treatment. Additionally, in a trial performed on normal controls, desipramine increased genioglossus activity and reduced upper airway collapsibility during sleep.

The selective norepinephrine reuptake inhibitor atomoxetine was tested by Bart-Sangal et al (2008, supra) in a prospective observational study of 15 patients with mild OSA. The drug did not improve AHI but did significantly improve daytime sleepiness. As shown herein, atomoxetine administered alone did not improve OSA severity in a sample of 9 moderate-to-severe OSA patients (Taranto-Montemurro et al. Am J Respir Crit Care Med 2019; 199:1267-1276).

In the last decade, animal[1, 2] and human[3] research has shown that noradrenergic withdrawal in the central nervous system plays a primary role in determining the upper airway dilator muscles hypotonia during sleep. Translational work performed recently in our laboratory showed that drugs with noradrenergic properties such as desipramine can increase genioglossus muscle activity[3] and can reduce upper airway collapsibility during sleep in humans[4]. However, our team and others have shown that noradrenergic drugs taken alone cannot reduce OSA severity. Protriptyline[5, 6], desipramine[4] and atomoxetine[7] have been tested in patients with OSA without success in reducing the AHI. Nevertheless, when atomoxetine was given in combination with the antimuscarinic oxybutynin, OSA severity was reduced by 63% compared to placebo in 20 unselected patients during a randomized double blinded crossover trial of a single night conducted in our lab[8]. Originally, the reason for combining oxybutynin to atomoxetine was to contrast the inhibitory mechanism mediated by muscarinic receptors that, according to Richard Horner's group[9], is responsible for the episodes of major suppression of genioglossus activity during REM sleep. Yet, the inhibitory role of muscarinic receptor is not supported by all animal research: for example Kubin et al. showed that in the anesthetized rat model the REM sleep-related depression of genioglossus activity can be fully explained by the combined withdrawal of two excitatory inputs: noradrenergic and serotonergic[10, 11].

A second possible mechanism at work in the combination of atomoxetine and oxybutynin is that oxybutynin could act as a hypnotic by increasing the arousal threshold and consolidating sleep, thus contrasting the wake-promoting effects of atomoxetine. Previous literature reported that antimuscarinics administered at low doses have mild sedative effects[12] and induce sleepiness[13]. Moreover, and consistently with this hypothesis, it has been also recently shown that oxybutynin can improve sleep quality by reducing symptoms of nocturia[14].

A low respiratory arousal threshold (wake up easily in response to upper airway obstruction) can limit neuromuscular compensation of the upper airway and contribute to the development of sleep-related hypopneas and apneas in many individuals. A reduction in ventilation during sleep during an obstructive apnea/hypopnea, leads to a buildup in $CO_2$ that increases ventilatory drive that can activate the pharyngeal muscles and reduce upper airway resistance by making the upper airway stiffer. A low respiratory arousal threshold, however, can preempt this important compensatory mechanism. Therefore, while for people with high arousal threshold the arousal is a life-saving mechanism to protect them from asphyxia during sleep, it may be destabilizing for patients with a low arousal threshold, because the premature awakening can perpetuate the cycle of repetitive upper airway collapse. Thus, preventing arousals with medications with specific profiles in patients taking a wake-activating drug like atomoxetine that induces a low arousal threshold, could yield more stable breathing and less OSA.

Notably, previous animal data showed that the administration of the antimuscarinic atropine could abolish the fast, low amplitude EEG activity induced by an adrenergic stimulant of the central nervous system (amphetamine) and induce low-frequency, high-amplitude brainwaves typical of NREM sleep[15]. Activating pharyngeal muscles with adrenergic drugs such as atomoxetine may be insufficient to treat OSA if the patients wake up for a minimal reduction in ventilation (namely: low arousal threshold). The concomitant administration of a potent sedative with a powerful activator of upper airway dilator muscles such as atomoxetine could lead to the pharmacological resolution of OSA in many patients.

Figure 2:
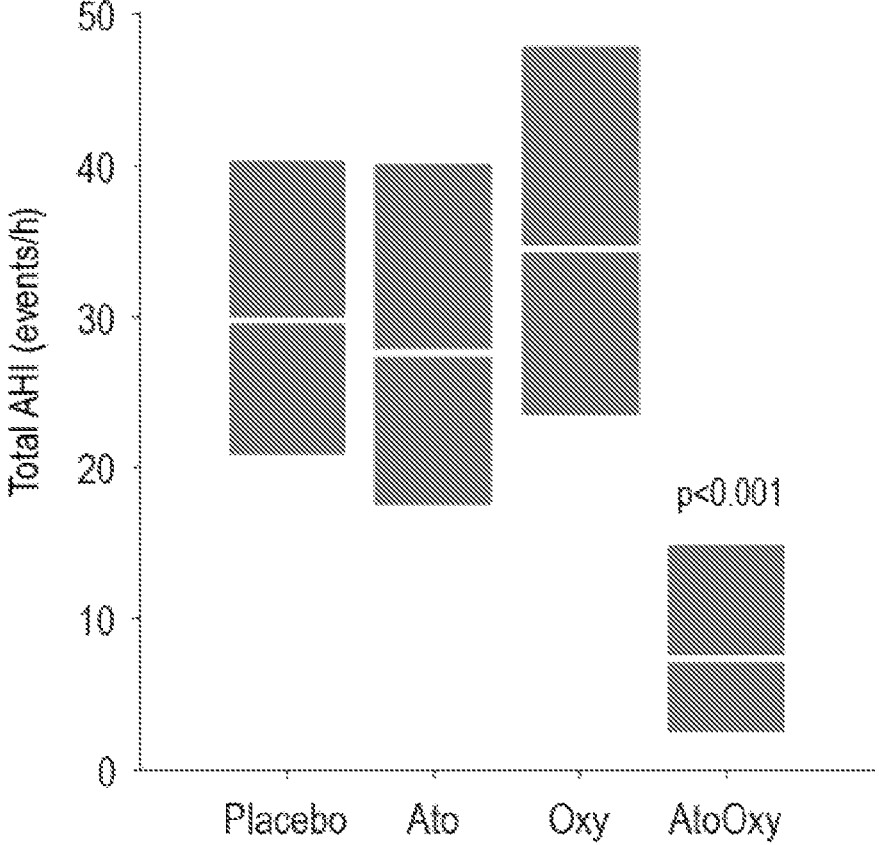
FIG. 2. Atomoxetine alone (Ato) and oxybutynin alone (Oxy) did not systematically reduce OSA severity (apnea hypopnea index, AHI). In contrast, there was a potent effect of these agents when administered together. White lines indicate means, boxes indicate 95% CI.
Figure 3A:
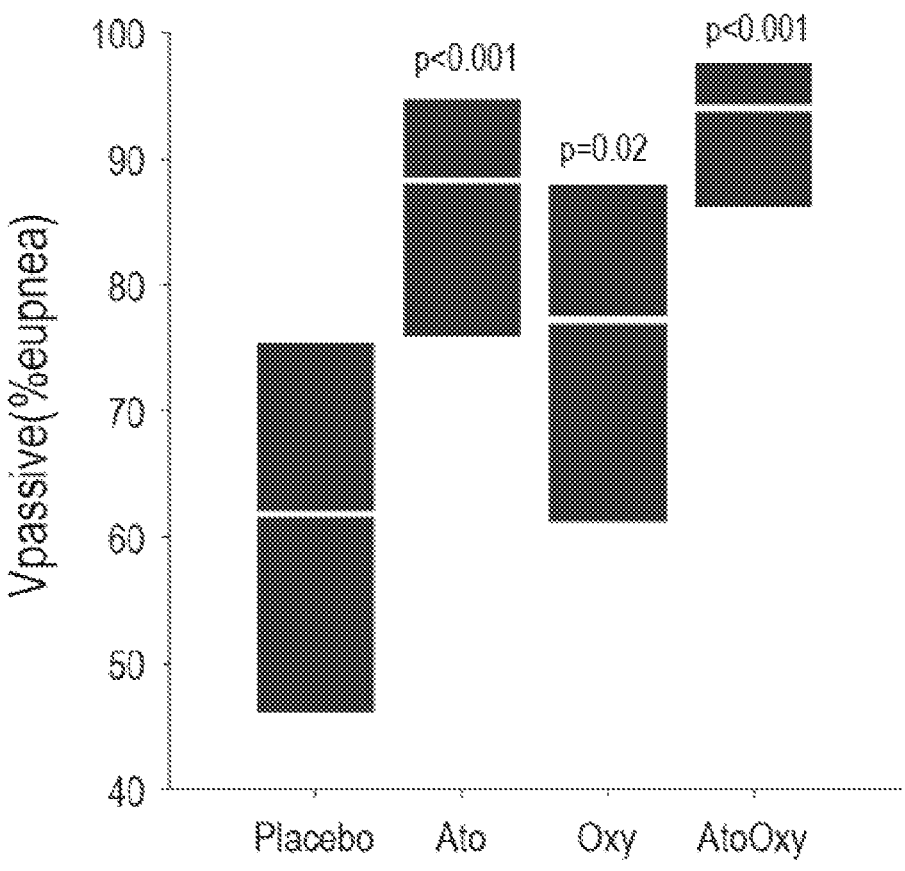
FIG. 3A-3B. Atomoxetine is responsible for most of the ventilatory improvement. Ventilation was measured during 'passive' condition (when ventilatory drive is close to eupneic level and the upper airway dilator muscles are relatively relaxed, 3A) and during 'active conditions' (when ventilatory drive is close to the arousal threshold and the upper airway muscles are close to the maximal activation possible during sleep, 3B). Vpassive is generally considered a measure of collapsibility of the upper airway. The increase in Vactive from atomoxetine to ato-oxy was likely due to an increase in arousal threshold (more time was allowed during sleep for muscle recruitment) rather than to the effect of oxybutynin.
Figure 3B:
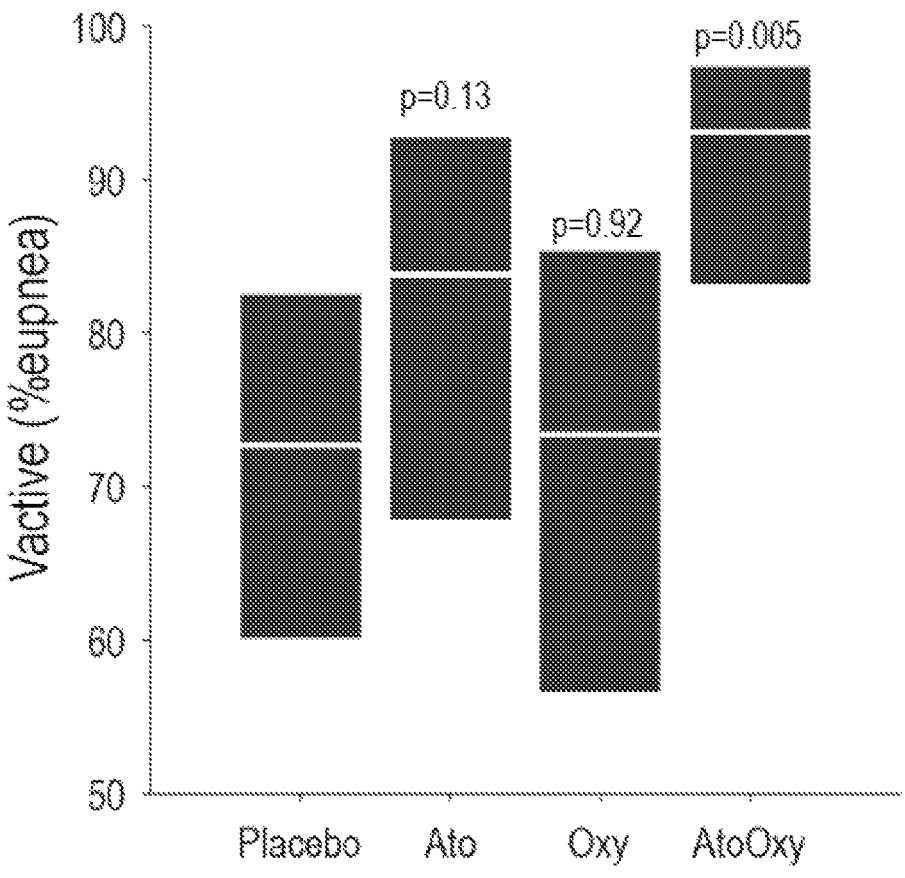

As described herein, although the contemporary administration of atomoxetine and oxybutynin reduced OSA severity (FIG. 2) in both REM and NREM sleep, when administered alone, atomoxetine and oxybutynin did not respectively improve NREM and REM specific AHI as originally hypothesized. An accurate analysis of ventilatory parameters during all night showed that atomoxetine alone accounted for at least 70% of the improvement in ventilation during sleep and improved oxygen saturation compared to placebo, while oxybutynin had a minor effect on ventilation and did not improve oxygen levels (FIGS. 3A-3B).

Figure 4:
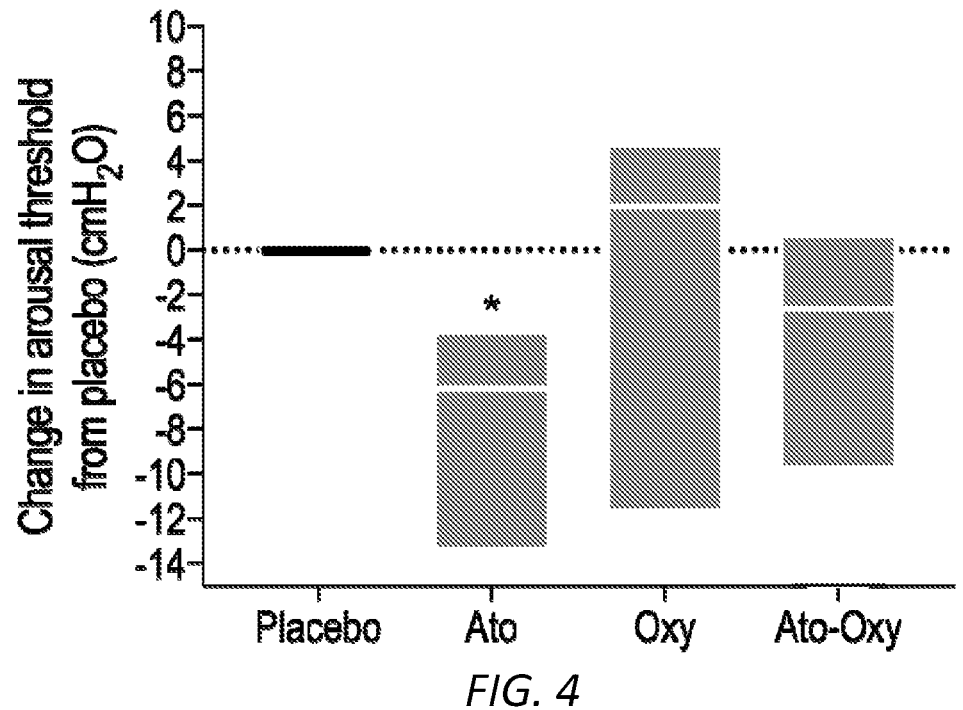
FIG. 4. Arousal threshold change from placebo to atomoxetine (ato), oxybutynin (oxy) and the drug combination (ato-oxy). *p=0.03 vs placebo and oxy.

Atomoxetine was responsible for a reduction in the arousal threshold (waking up more easily), likely because of its adrenergic properties. However, when atomoxetine was administered with oxybutynin, the reduction in arousal threshold with the combination was a non-statistically-significant 7% (p>0.7, FIG. 4). These data suggest that the most important effect of oxybutynin in the combination was to attenuate the alerting effect of atomoxetine.

This unexpected finding suggested that oxybutynin could be replaced by non myorelaxing hypnotics with a more powerful effect on the arousal threshold such as z-drugs (i.e. zolpidem, zopiclone) or agents enhancing sleep depth and slow wave sleep (i.e. gabapentin, tiagabine). The effect of zolpidem and other commonly used hypnotics (zopiclone, temazepam) on genioglossus muscle activity and arousal threshold has been recently tested in 21 subjects with and without OSA by Carberry et al. Amongst the hypnotics tested, zolpidem improved the arousal threshold by ~30% and, unexpectedly, increased also the median genioglossus muscle responsiveness by 3-fold (p=0.03) compared to placebo[16].

As described herein, drugs that increase sleep depth (and slow wave sleep (SWS) in particular) such as tiagabine or gabapentin could help the resolution of OSA. We administered the anti-epileptic drug tiagabine to 14 OSA subjects without worsening the AHI or the oxygen saturation during sleep in these patients[17]. EEG showed an increase in slow wave activity by 16% suggesting that the drug mildly increased sleep depth. The pharmacological increase in slow wave sleep (SWS) could be an ideal mechanism for raising the arousal threshold to treat OSA, particularly since SWS seems to be a "protective state" against OSA. Ratnavadivel et al. found that 82% of patients with moderate to severe OSA achieve an AHI<15 events/hr in SWS[18]. The reason for improvement likely relates to changes in the non-anatomical factors that contribute to OSA during SWS such as reduced arousability, thereby enabling a higher activation of upper airway dilator muscles. Furthermore, we recently showed that, after inducing a reflex activation of the genioglossus muscle with a transient obstruction of the upper airway during sleep, the time during which the activity of the genioglossus remained elevated above baseline after the obstructive stimulus was removed (also called after-discharge, see FIG. 5) was 2-fold longer during SWS compared to NREM 2 sleep. These data suggest that a form of neural memory of the upper airway dilator muscles is in place and may help to stiffen the pharynx and stabilize breathing selectively during SWS in OSA[19]. Thus, as described herein, drugs such as gabapentin that cause 20-60% increase of SWS[20,21], are ideal candidates for the treatment of OSA in association with atomoxetine.

Serotonin neurons in the brainstem are critical for producing both the cortical and respiratory motor response to hypercapnia. Serotonin neuron deficient mice have an impaired hypercapnic ventilatory response (HCVR)[26] and lack the ability to arouse from sleep in response to $CO_2$[27]. Buchanan was able to restore the EEG arousal in these mice with 5-HT2A receptor stimulation, suggesting that this specific sub-receptor is responsible for activating the central nervous system in response to chemosensory (respiratory) stimuli. This notion is supported by human data; Heinzer et al.[28] showed that administration of trazodone 100 mg (a 5-HT2A antagonist) before bedtime to eight OSA patients increased the arousal threshold in response to hypercapnia, allowing tolerance of higher CO2 levels without arousal. Eckert et al.[29] showed that trazodone could improve arousal threshold by 30% in seven patients with a low arousal threshold, but it did not affect the AHI compared to placebo. By contrast, Smales et al.[30] showed that trazodone 100 mg reduced the AHI by 26% in 15 unselected OSA patients.

Other hypnotics and sedatives were previously tested in OSA patients (zolpidem, zopiclone, eszopiclone, temazepam, tiagabine) to increase the arousal threshold. These sedatives, rather than targeting the 5-HT2A receptor, act by activating the GABA receptors and by reducing the general excitability of the central nervous system and could be also used in combination with atomoxetine and other noradrenergic agents to reduce OSA severity.

In a physiology trial including 21 individuals with and without OSA, 10 mg of zolpidem increased the arousal threshold by 25% and, unexpectedly, also the genioglossus response to pharyngeal negative pressure as compared to placebo[33]. Among other Z-drugs, eszopiclone and zopiclone were studied in OSA patients to measure their effect on the arousal threshold. Eckert et al[34], in a 1-night crossover trial including 17 OSA patients, showed that eszopiclone increased the arousal threshold by ~30%. Although the group data did not show a significant reduction in AHI overall, those with a low arousal threshold at baseline (8/17) had their AHI reduced by 43%. Carter et al[35] showed that zopiclone 7.5 mg administered for 1 night (n=12) increased the arousal threshold by 20% but did not significantly change the AHI compared to placebo. A subsequent parallel-arm trial from the same group, testing zopiclone (n=14) vs placebo (n=16), showed a non-significant reduction in AHI between the two groups (−25% from baseline and −15% from placebo) after 30 days of treatment[36]. In a four-arm trial by Carberry and coworkers[33] zopiclone 7.5 mg significantly increased arousal threshold (but did not change AHI) vs placebo in a group of 21 healthy individuals and OSA patients.

Methods of Treatment

The methods described herein include methods for the treatment of disorders associated with pharyngeal airway muscle collapse during sleep. In some embodiments, the disorder is Obstructive Sleep Apnea (OSA) (defined as an AHI of ≥10 events per hour) or Simple Snoring. Generally, the methods include administering a therapeutically effective amount of (i) a norepinephrine reuptake inhibitor and (ii) a non myorelaxing hypnotic agent and/or 5-HT2A inverse agonist or antagonist as known in the art and/or described herein, to a subject who is in need of, or who has been determined to be in need of, such treatment.

As used in this context, to "treat" means to ameliorate at least one symptom of the disorder associated with pharyngeal airway collapse. Often, pharyngeal airway collapse during sleep results in snoring and/or an interruption in breathing (apnea or hypopnea), arousal from sleep, and reduced oxygenation (hypoxemia); thus, a treatment can result in a reduction in one or more of snoring, apneas/hypopneas, sleep fragmentation, and hypoxemia.

Unexpectedly, administration of a therapeutically effective amount of a norepinephrine reuptake inhibitor and a non myorelaxing hypnotic agent and/or 5-HT2A inverse agonist or antagonist for the treatment of a subject having a condition associated with pharyngeal airway collapse while the subject is in a non-fully conscious state, such as OSA, will result in decreased AHI. In some embodiments, the administration of a therapeutically effective amount of a norepinephrine reuptake inhibitor and a non myorelaxing hypnotic agent and/or 5-HT2A inverse agonist or antagonist for the treatment of a subject having a condition associated with pharyngeal airway collapse while the subject is in a non-fully conscious state, such as OSA, will result in decreased AHI by 50% or more. In some embodiments, the administration of a therapeutically effective amount of a norepinephrine reuptake inhibitor and a non myorelaxing hypnotic agent and/or 5-HT2A inverse agonist or antagonist for the treatment of a subject having a condition associated with pharyngeal airway collapse while the subject is in a non-fully conscious state, such as OSA, will result in decreased AHI by 75% or more. In other further embodiments, the administration of a therapeutically effective amount of a norepinephrine reuptake inhibitor and a non myorelaxing hypnotic agent and/or 5-HT2A inverse agonist or antagonist for the treatment of a subject having a condition associated with pharyngeal airway collapse while the subject is in a non-fully conscious state, such as OSA, will result in increased ventilation. In yet other embodiments, the administration of a therapeutically effective amount of a norepinephrine reuptake inhibitor and a non myorelaxing hypnotic agent and/or 5-HT2A inverse agonist or antagonist for the treatment of a subject having a condition associated with pharyngeal airway collapse while the subject is in a non-fully conscious state, such as OSA, will result in increased oxygen blood levels. In still another embodiment, the administration of a therapeutically effective amount of a norepinephrine reuptake inhibitor and a non myorelaxing hypnotic agent and/or 5-HT2A inverse agonist or antagonist for the treatment of a subject having a condition associated with pharyngeal airway collapse while the subject is in a non-fully conscious state, such as OSA, will result in improved total sleep time, reduced AHI, increased oxygenation, less sleep fragmentation, increased total sleep time, and/or improved subjective sleep quality.

An effective amount of a norepinephrine reuptake inhibitor and a non myorelaxing hypnotic agent can be administered in one or more administrations, applications or dosages, simultaneously or separately. When administered simultaneously, a norepinephrine reuptake inhibitor and a non myorelaxing hypnotic agent and/or 5-HT2A inverse agonist or antagonist can be formulated as a single dosage form, e.g., a capsule, tablet or solution, containing both a norepinephrine reuptake inhibitor and a non myorelaxing hypnotic agent, or as separate dosage forms, e.g., one a capsule, tablet or solution, containing a norepinephrine reuptake inhibitor and another capsule, tablet or solution containing a non myorelaxing hypnotic agent and/or 5-HT2A inverse agonist or antagonist. Each of the norepinephrine reuptake inhibitor and the non myorelaxing hypnotic agents and/or 5-HT2A inverse agonist or antagonist can be administered, simultaneously or separately from one or more times per day to one or more times per week; including once every other day. In some embodiments, the norepinephrine reuptake inhibitor and the non myorelaxing hypnotic agent and/or 5-HT2A inverse agonist or antagonist are administered daily. In some embodiments, the agents are administered less than 60, 45, 30, 20, or 15 minutes before a subject wishes or intends to fall asleep. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

Dosage, toxicity and therapeutic efficacy of the therapeutic compounds (i.e., NRI and non myorelaxing hypnotic and/or 5-HT2A inverse agonist or antagonist, in a single composition or in separate compositions) can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50.

The data obtained from cell culture assays and animal studies can be used in formulating a range of dosages for use in humans. The dosage of such compounds lies preferably within a range of circulating concentrations that include the ED50 with little or no toxicity. The dosage may vary within this range depending upon the dosage form employed and the route of administration utilized. The therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

In some embodiments, the methods include administering a dose of 20-100 mg Atomoxetine (or a dose equivalent thereof of another NRI) and a dose of 2-12.5 mg zolpidem, e.g., extended release zolpidem (or a dose equivalent thereof of another non myorelaxing hypnotic). In some embodiments, the methods include administering 80 mg Atomoxetine/12.5 mg zolpidem; 75 mg Atomoxetine/10 mg zolpidem; 75 mg Atomoxetine/8 mg zolpidem; 50 mg Atomoxetine/6 mg zolpidem; or 25 mg Atomoxetine/4 mg zolpidem. In other embodiments, the methods include administering a dose of 20-100 mg Atomoxetine (or a dose equivalent thereof of another NRI) and a dose of 2-12 mg zolpidem (or a dose equivalent thereof of another non myorelaxing hypnotic) within an hour of sleep time. In some embodiments, the methods include administering 80 mg Atomoxetine/12 mg zolpidem; 75 mg Atomoxetine/10 mg zolpidem; 75 mg Atomoxetine/8 mg zolpidem; 50 mg Atomoxetine/6 mg zolpidem; or 25 mg Atomoxetine/4 mg zolpidem, 15-10 minutes before sleep time.

In further embodiments, the methods include administering Atomoxetine/zolpidem in a 6.5 to 1 ratio by weight. In other embodiments, the methods include administering Atomoxetine/zolpidem in a 6.5 to 1 ratio by weight at 15-10 minutes before sleep time.

In some embodiments, Gabapentin, e.g., 600 mg gabapentin, is used in place of zolpidem. In some embodiments, pimvanserin, e.g., 20-40 mg, e.g., 34 mg pimvanserin, is used in addition to or in place of zolpidem.

Pharmaceutical Compositions and Methods of Administration

The methods described herein include the use of pharmaceutical compositions comprising a norepinephrine reuptake inhibitor and a non myorelaxing hypnotic agent and/or 5-HT2A inverse agonist or antagonist as active ingredients. The norepinephrine reuptake inhibitor and non myorelaxing hypnotic agent and/or 5-HT2A inverse agonist or antagonist can be administered in a single composition or in separate compositions. In some embodiments, the methods include administering a norepinephrine reuptake inhibitor and a non myorelaxing hypnotic agent and/or 5-HT2A inverse agonist or antagonist, and no other active ingredients, i.e., the norepinephrine reuptake inhibitor and the non myorelaxing hypnotic agent and/or 5-HT2A inverse agonist or antagonist are the sole active agents.

Exemplary norepinephrine reuptake inhibitors (NRIs) include the selective NRIs, e.g., Amedalin (UK-3540-1), Atomoxetine (Strattera), CP-39,332, Daledalin (UK-3557-

15), Edivoxetine (LY-2216684), Esreboxetine, Lortalamine (LM-1404), Nisoxetine (LY-94,939), Reboxetine (Edronax, Vestra), Talopram (Lu 3-010), Talsupram (Lu 5-005), Tandamine (AY-23,946), Viloxazine (Vivalan); and the non-selective NRIs, e.g., Amitriptiline, Amoxapine, Bupropion, Ciclazindol, Desipramine, Desvenlafaxine, Dexmethylphenidate, Diethylpropion, Doxepin, Duloxetine, Imipramine, Levomilnacipran, Manifaxine (GW-320,659), Maprotiline, Methylphenidate, Milnacipran, Nefazodone, Nortriptyline, Phendimetrazine, Phenmetrazine, Protryptyline, Radafaxine (GW-353,162), Tapentadol (Nucynta), Teniloxazine (Lucelan, Metatone) and Venlafaxine.

Suitable, but non-limiting, examples of non myorelaxing hypnotics include a benzodiazepine hypnotic, e.g., temazepam, brotizolam, flurazepam, nitrazepam, or triazolam; or a non-benzodiazepine hypnotic, e.g., a cyclopyrrolone hypnotic, preferably selected from the group consisting of zolpidem, zopiclone, and eszopiclone; gabapentin; trazodone; diphenhydramine; suvorexant; tasimelteon; ramelteon; agomelatine; doxepin; zaleplon; doxylamine; sodium oxybate; or tiagabine.

Exemplary 5-HT2A inverse agonists include AC-90179 (Weiner et al., The Journal of Pharmacology and Experimental Therapeutics. 299 (1): 268-76), ketanserin, nelotanserin, eplivanserin, pimavanserin, and volinanserin; antagonists include Trazodone, Mirtazapine, ketanserin, clozapine, olanzapine, quetiapine, risperidone, iloperidone, perospirone, asenapine, nefazodone, MDL-100,907, cyproheptadine, pizotifen, LY-367,265, 2-alkyl-4-aryl-tetrahydro-pyrimido-azepines, haloperidol, chlorpromazine, hydroxyzine (Atarax), 5-MeO-NBpBrT, and niaprazine. In some embodiments, the 5-HT2A antagonist is ketanserin, iloperidone, perospirone, risperdone or nefazodone.

In some embodiments, the norepinephrine reuptake inhibitor is Atomoxetine. In some embodiments, the non myorelaxing hypnotic is zolpidem. In some embodiments, the 5-HT2A inverse agonist is pimvanserin.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions, however the present compositions do not include an antimuscarinic agent (e.g., as described in WO 2018/200775).

Pharmaceutical compositions are typically formulated to be compatible with their intended route of administration. Examples of routes of administration include systemic oral or transdermal administration.

Methods of formulating suitable pharmaceutical compositions are known in the art, see, e.g., Remington: The Science and Practice of Pharmacy, 21st ed., 2005; and the books in the series Drugs and the Pharmaceutical Sciences: a Series of Textbooks and Monographs (Dekker, NY). For example, oral compositions generally include an inert diluent or an edible carrier. For the purpose of oral therapeutic administration, the active compound(s) can be incorporated with excipients and used in the form of pills, tablets, troches, or capsules, e.g., gelatin capsules. Oral compositions can also be prepared using a fluid carrier. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Systemic administration of one or both of the compounds as described herein (i.e., one or both of a norepinephrine reuptake inhibitor and a non myorelaxing hypnotic) can also be by transdermal means, e.g., using a patch, gel, lotion, or thin film, to be applied to the skin. For transdermal administration, penetrants appropriate to the permeation of the epidermal barrier can be used in the formulation. Such penetrants are generally known in the art. For example, for transdermal administration, the active compounds can be formulated into ointments, salves, gels, or creams as generally known in the art. The gel and/or lotion can be provided in individual sachets, or via a metered-dose pump that is applied daily; see, e.g., Cohn et al., Ther Adv Urol. 2016 April; 8 (2): 83-90.

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration or use in a method described herein.

EXAMPLES

The invention is further described in the following examples, which do not limit the scope of the invention described in the claims.

Example 1

In a preliminary investigation, nine patients equipped with a pneumotachograph attached to an oronasal mask to measure ventilation and an esophageal catheter to estimate the arousal threshold, performed a sleep study on each of these 4 conditions: placebo, atomoxetine alone, oxybutynin alone and ato-oxy. Although the contemporary administration of atomoxetine and oxybutynin reduced OSA severity (FIG. 2) in both REM and NREM sleep, when administered alone, atomoxetine and oxybutynin did not respectively improve NREM and REM specific AHI as originally hypothesized. An accurate analysis of ventilatory parameters during all night showed that atomoxetine alone accounted for at least 70% of the improvement in ventilation during sleep and improved oxygen saturation compared to placebo, while oxybutynin had a minor effect on ventilation (FIGS. 3A-3B) and did not improve oxygen levels. Unfortunately, atomoxetine was responsible of a reduction in the arousal threshold (waking up more easily) by 18% (p=0.03) vs placebo, likely because of its adrenergic properties. However, when atomoxetine was administered with oxybutynin, the reduction in arousal threshold with the combination was a non-statistically-significant 7% (p>0.7, FIG. 4). These data suggest that the most important effect of oxybutynin in the combination was to attenuate the alerting effect of atomoxetine.

Furthermore, after inducing a reflex activation of the genioglossus muscle with a transient obstruction of the upper airway during sleep, the time during which the activity of the genioglossus remained elevated above baseline after the obstructive stimulus was removed (also called after-discharge, see FIGS. 5A-B and Ref 19) was 2-fold longer during slow wave sleep (SWS) compared to NREM 2 sleep. These data suggest that a form of neural memory of the upper airway dilator muscles is in place and may help to stiffen the pharynx and stabilize breathing selectively during SWS in OSA19.

Example 2

Pilot Study

Subjects

OSA subjects with a broad range of apnea severity (10 to >60/hr) are studied in a double blinded, placebo controlled, crossover trial. Treated OSA patients are enrolled, since we do not want to delay treatment to perform these experiments. These individuals are otherwise healthy (except for well-controlled hypertension, diabetes, or hyperlipidemia) with no active medical problems and on no medication that could affect respiration or muscle control. Subjects are 21-70 years old. Both men and women will have an apnea-hypopnea index (AHI) >10 events/hr during supine NREM sleep.

Equipment

Subjects are instrumented with standard polysomnography (PSG) recording sensors. Sleep stage and arousals are measured with electrodes pasted on to the scalp, face, chin, and chest (EEG, EOG, EKG, chin EMG). Paste-on EMG electrodes are placed over the anterior tibialis muscle to detect leg movements. Respiratory effort belts are placed around the chest and abdomen to measure breathing movements. Oxygen saturation is measured continuously with a pulse oximetry probe placed on the fingertip. Snoring is detected with a small microphone positioned over the suprasternal notch. Body position is recorded with a sensor taped to the thoracic belt. Each of these devices is standard for diagnostic PSG and should not be uncomfortable. To measure airflow, a standard CPAP mask is placed over the mouth and the nose and held in place with straps. The mask allows monitoring of breathing (inspiratory flow by pneumotachograph that can be integrated to yield tidal volume) and expired carbon dioxide levels ($PCO_2$) using a calibrated infrared $CO_2$ analyzer (Capnograph/Oximeter Monitor).

Protocol

We test the effect of a study treatment on OSA severity, administering to OSA patients in random order:

1) atomoxetine 80 mg+zolpidem 10 mg;
2) atomoxetine 80 mg+diphenhydramine 50 mg;
3) atomoxetine 80 mg+trazodone 100 mg;
4) atomoxetine 80 mg+gabapentin 300 mg; or
5) placebo.

After a baseline polysomnography, an in-laboratory overnight sleep study on the 3rd day of treatment is performed approximately one week apart in random order. Two pills of placebo or drug combinations are administered 15 minutes before lights out. At least 5 minutes of quiet wakefulness are recorded to quantify the subject's awake ventilation. As much data are recorded from NREM and REM sleep as possible over the night. Patients are asked to sleep in the supine position at least for 50% of the night.

Data Analysis

Apneas, hypopneas, arousals, and sleep stages are scored using standard American Academy of Sleep Medicine guidelines[22] by a registered polysomnographic technologist (RPSGT) blinded to the treatment allocation. Hypopneas are defined as reduction in flow ≥30% from baseline, lasting at least 10 seconds and associated with an arousal from sleep or an oxyhemoglobin desaturation ≥3%. Phenotypic traits (Vpassive, Vactive, arousal threshold, loop gain) on placebo and on drug nights are automatically calculated from the polysomnography using the algorithms developed and tested in our lab[23, 24].

The main outcome of the trial is the change in AHI and it is compared between the arms using a one-way anova followed by post-hoc analysis to compare each treatment arm with placebo, with p<0.025 considered as statistically significant in order to correct for multiple comparisons. Each individual requires four studies (baseline+3 trial nights).

Hypothesized Results

The drugs combinations tested are evaluated for a meaningful reduction in in OSA severity (AHI), an increase in oxygen levels (SaO$_2$), and a reduction in collapsibility (Vpassive and Vactive) in both NREM and REM sleep. The results are interpreted to determine whether it is possible to improve sleep apnea severity and sleep quality with a combination of systemically administered drugs in sleeping humans. The analysis of the phenotypic traits during the baseline night provides information on what group of patients is likely to have the best response on the drugs, the phenotypic analysis on the placebo and drugs night will inform about the mechanisms of action of these combinations.

Example 3

Alternative Hypnotic Agents

To determine whether other non-myorelaxing hypnotic agents could be used in place of zolpidem or gabapentin, further trials using zopiclone, eszopiclone, trazodone, or diphenhydramine are used in combination with 80 mg Atomoxetine in subjects with a mild to moderate upper airway collapsibility (ventilation during sleep with normal effort was above 50% of eupneic ventilation on placebo). Effects on OSA severity (AHI), oxygen levels (SaO$_2$), and airway collapsibility (Vpassive and Vactive) are evaluated in both NREM and REM sleep.

Example 4

Combination of Atomoxetine and Pimavanserin for the Treatment of OSA

We administered the recently-approved selective 5-HT2A inverse agonist pimavanserin 34 mg to block the EEG arousal response to CO$_2$ in association with atomoxetine 80 mg and measured the effect of this combination on OSA severity, arousal threshold and collapsibility in 5 patients. These doses were chosen as they are the usual effective doses for attention-deficit disorder and delusion-hallucinations in patients with Parkinson's disease, respectively, based on prescribing information. Patients were also instrumented with an oronasal mask, and in 4/5 patients, esophageal catheter and genioglossus intramuscular electrodes.

16

Figure 6:
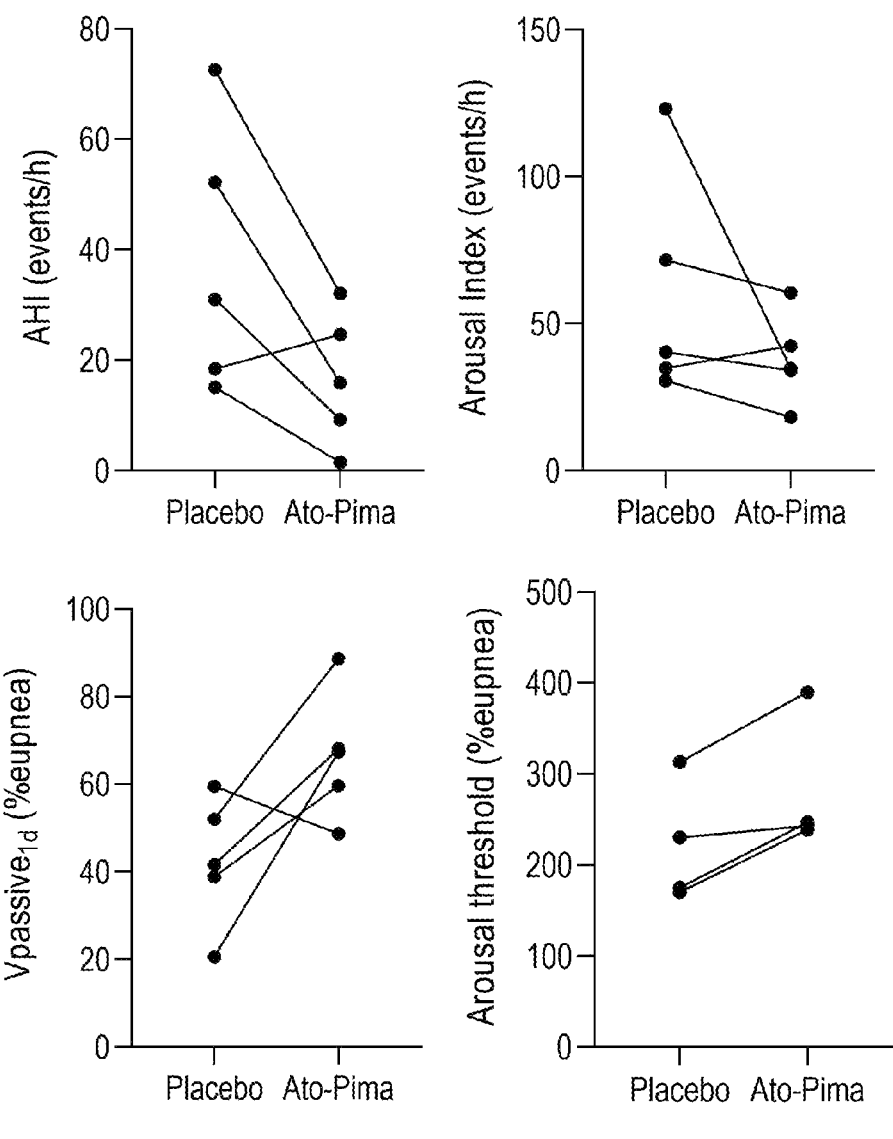
FIG. 6. The effect of the combination of Atomoxetine-Pimavanserin (Ato-Pima) on OSA severity (apnea hypopnea index, AHI), on the arousal index, the upper airway collapsibility (ventilation at low ventilatory drive, Vpassive) and the arousal threshold.

Atomoxetine-plus-pimavanserin markedly reduced the AHI from a median [interquartile range] of 31 [34] to 16 [15] events/hour (median change: 70 [15]%), improved upper airway collapsibility (Vpassive$_{ld}$) by 63 [28]%eupnea (p=0.07), increased the arousal threshold by 32 [20]% (FIG. 6) and increased the genioglossus activity by 110 [244]%. The effect on the arousal threshold is noteworthy, because pimavenserin was administered together with atomoxetine, a wake-promoting drug that, as described above, caused a reduction in arousal threshold by ~18% compared to placebo in OSA patients in a previous trial. This means that pimavanserin could actually increase the respiratory arousal threshold by ~50%.

REFERENCES

1. Chan E, Steenland H W, Liu H, Horner R L. Endogenous excitatory drive modulating respiratory muscle activity across sleep-wake states. *American journal of respiratory and critical care medicine.* 2006; 174:1264-1273
2. Song G, Poon C S. Alpha2-adrenergic blockade rescues hypoglossal motor defense against obstructive sleep apnea. *JCI Insight.* 2017; 2:e91456
3. Taranto-Montemurro L, Edwards B A, Sands S A, Marques M, Eckert D J, White D P, Wellman A. Desipramine increases genioglossus activity and reduces upper airway collapsibility during non-rem sleep in healthy subjects. *American journal of respiratory and critical care medicine.* 2016; 194:878-885
4. Taranto-Montemurro L, Sands S A, Edwards B A, Azarbarzin A, Marques M, de Melo C, Eckert D J, White D P, Wellman A. Desipramine improves upper airway collapsibility and reduces osa severity in patients with minimal muscle compensation. *The European respiratory journal.* 2016; 48:1340-1350
5. Brownell L G, West P, Sweatman P, Acres J C, Kryger M H. Protriptyline in obstructive sleep apnea: A double-blind trial. *N Engl J Med.* 1982; 307:1037-1042
6. Smith P L, Haponik E F, Allen R P, Bleecker E R. The effects of protriptyline in sleep-disordered breathing. *The American review of respiratory disease.* 1983; 127:8-13
7. Bart Sangal R, Sangal J M, Thorp K. Atomoxetine improves sleepiness and global severity of illness but not the respiratory disturbance index in mild to moderate obstructive sleep apnea with sleepiness. *Sleep Med.* 2008; 9:506-510
8. Taranto-Montemurro L, Messineo L, Sands S A, Azarbarzin A, Marques M, Edwards B A, Eckert D J, White D P, Wellman A. The combination of atomoxetine and oxybutynin greatly reduces obstructive sleep apnea severity: A randomized, placebo-controlled, double-blind crossover trial. *American journal of respiratory and critical care medicine.* 2018
9. Grace K P, Hughes S W, Horner R L. Identification of the mechanism mediating genioglossus muscle suppression in rem sleep. *American journal of respiratory and critical care medicine.* 2013; 187:311-319
10. Kubin L. Neural control of the upper airway: Respiratory and state-dependent mechanisms. *Comprehensive Physiology.* 2016; 6:1801-1850
11. Fenik V B, Davies R O, Kubin L. Rem sleep-like atonia of hypoglossal (xii) motoneurons is caused by loss of noradrenergic and serotonergic inputs. *American journal of respiratory and critical care medicine.* 2005; 172: 1322-1330
12. Thornton W E. Sleep aids and sedatives. *JACEP.* 1977; 6:408-412

13. Weerts A P, Pattyn N, Putcha L, Hoag S W, Van Ombergen A, Hallgren E, Van de Heyning P H, Wuyts F L. Restricted sedation and absence of cognitive impairments after administration of intranasal scopolamine. *J Psychopharmacol.* 2015; 29:1231-1235

14. Yokoyama O, Yamaguchi A, Yoshida M, Yamanishi T, Ishizuka O, Seki N, Takahashi S, Yamaguchi O, Higo N, Minami H, Masegi Y. Once-daily oxybutynin patch improves nocturia and sleep quality in japanese patients with overactive bladder: Post-hoc analysis of a phase iii randomized clinical trial. *Int J Urol.* 2015; 22:684-688

15. White R P, Daigneault E A. The antagonisms of atropine to the eeg effects of adrenergic drugs. *The Journal of pharmacology and experimental therapeutics.* 1959; 125: 339-346

16. Carberry J C, Fisher L P, Grunstein R R, Gandevia S C, McKenzie D K, Butler J E, Eckert D J. Role of common hypnotics on the phenotypic causes of obstructive sleep apnoea: Paradoxical effects of zolpidem. *The European respiratory journal.* 2017; 50

17. Taranto-Montemurro L, Sands S A, Edwards B A, Azarbarzin A, Marques M, De Melo C, Eckert D J, White D P, Wellman A. Effects of tiagabine on slow wave sleep and arousal threshold in patients with obstructive sleep apnea. *Sleep.* 2017; 40

18. Ratnavadivel R, Chau N, Stadler D, Yeo A, McEvoy R D, Catcheside P G. Marked reduction in obstructive sleep apnea severity in slow wave sleep. *J Clin Sleep Med.* 2009; 5:519-524

19. Taranto-Montemurro L, Sands S A, Grace K P, Azarbarzin A, Messineo L, Salant R, White D P, Wellman D A. Neural memory of the genioglossus muscle during sleep is stage-dependent in healthy subjects and obstructive sleep apnoea patients. *The Journal of physiology.* 2018; 596:5163-5173

20. Foldvary-Schaefer N, De Leon Sanchez I, Karafa M, Mascha E, Dinner D, Morris H H. Gabapentin increases slow-wave sleep in normal adults. *Epilepsia.* 2002; 43:1493-1497

21. Rao M L, Clarenbach P, Vahlensieck M, Kratzschmar S. Gabapentin augments whole blood serotonin in healthy young men. *J Neural Transm.* 1988; 73:129-134

22. Berry R B, Budhiraja R, Gottlieb D J, Gozal D, Iber C, Kapur V K, Marcus C L, Mehra R, Parthasarathy S, Quan S F, Redline S, Strohl K P, Davidson Ward S L, Tangredi M M, American Academy of Sleep M. Rules for scoring respiratory events in sleep: Update of the 2007 aasm manual for the scoring of sleep and associated events. Deliberations of the sleep apnea definitions task force of the american academy of sleep medicine. *J Clin Sleep Med.* 2012; 8:597-619

23. Sands S A, Edwards B A, Terrill P I, Taranto-Montemurro L, Azarbarzin A, Marques M, Hess L B, White D P, Wellman A. Phenotyping pharyngeal pathophysiology using polysomnography in patients with obstructive sleep apnea. *American journal of respiratory and critical care medicine.* 2018; 197:1187-1197

24. Sands S A, Terrill P I, Edwards B A, Taranto Montemurro L, Azarbarzin A, Marques M, de Melo C M, Loring S H, Butler J P, White D P, Wellman A. Quantifying the arousal threshold using polysomnography in obstructive sleep apnea. *Sleep.* 2018; 41

25. Brownell L G, West P, Sweatman P, et al. Protriptyline in obstructive sleep apnea: a double-blind trial. N Engl J Med 1982; 307:1037-1042

26 Hodges M R, Tattersall G J, Harris M B, et al. Defects in breathing and thermoregulation in mice with near-complete absence of central serotonin neurons. *J Neurosci* 2008; 28:2495-2505

27 Buchanan G F, Smith H R, MacAskill A, et al. 5-HT2A receptor activation is necessary for CO2-induced arousal. J Neurophysiol 2015; 114:233-243

28 Heinzer R C, White D P, Jordan A S, et al. Trazodone increases arousal threshold in obstructive sleep apnoea. Eur Respir J 2008; 31:1308-1312

29 Eckert D J, Malhotra A, Wellman A, et al. Trazodone increases the arousal threshold in obstructive sleep apnea patients with a low arousal threshold. Sleep 2014; 37:811-819

30 Smales E T, Edwards B A, Deyoung P N, et al. Trazodone Effects on Obstructive Sleep Apnea and Non-REM Arousal Threshold. Ann Am Thorac Soc 2015; 12:758-764

31 Taranto-Montemurro L, Messineo L, Wellman A. Targeting Endotypic Traits with Medications for the Pharmacological Treatment of Obstructive Sleep Apnea. A Review of the Current Literature. J Clin Med 2019; 8

32 Carberry J C, Grunstein R R, Eckert D J. The effects of zolpidem in obstructive sleep apnea—An open-label pilot study. J Sleep Res 2019:e12853

33 Carberry J C, Fisher L P, Grunstein R R, et al. Role of common hypnotics on the phenotypic causes of obstructive sleep apnoea: paradoxical effects of zolpidem. Eur Respir J 2017; 50

34 Eckert D J, Owens R L, Kehlmann G B, et al. Eszopiclone increases the respiratory arousal threshold and lowers the apnoea/hypopnoea index in obstructive sleep apnoea patients with a low arousal threshold. Clin Sci (Lond) 2011; 120:505-514

35 Carter S G, Berger M S, Carberry J C, et al. Zopiclone Increases the Arousal Threshold without Impairing Genioglossus Activity in Obstructive Sleep Apnea. Sleep 2016; 39:757-766

36 Carter S G, Carberry J C, Cho G, et al. Effect of 1 month of zopiclone on obstructive sleep apnoea severity and symptoms: a randomised controlled trial. Eur Respir J 2018; 52

37 Carter S, Carberry J, Grunstein R, et al. High dose zopiclone does not change osa severity, the respiratory arousal threshold, genioglossus muscle responsiveness or next-day sleepiness and alertness in selected people with OSA. Presented in the form of Abstract at World Sleep 2019, Vancouver, Canada. 2019

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a disease or disorder selected from sleep apnea or snoring in a subject in need thereof, comprising administering to the subject an effective amount of (i) atomoxetine and (ii) pimavanserin.

2. The method of claim 1, wherein the atomoxetine is administered at a dose of 20 to 100 mg.

3. The method of claim 1, wherein the pimavanserin is administered at a dose of 20 to 40 mg.

4. The method of claim 1, wherein the disease or disorder is sleep apnea.

5. The method of claim 4, wherein the disease or disorder is obstructive sleep apnea.

6. The method of claim 1, wherein the subject is in a non-fully conscious state, and wherein the non-fully conscious state is sleep.

7. The method of claim 1, wherein the atomoxetine and the pimavanserin are administered in a single composition, wherein the single composition is an oral administration form.

\*    \*    \*    \*    \*